United States Patent [19]
Lowe et al.

[11] Patent Number: 6,028,055
[45] Date of Patent: Feb. 22, 2000

[54] RECEPTOR SELECTIVE BNP

[75] Inventors: David G. Lowe, Hillsborough; Jill R. Schoenfeld, Burlingame, both of Calif.

[73] Assignee: Genetech, Inc., South San Francisco, Calif.

[21] Appl. No.: 08/954,915

[22] Filed: Oct. 21, 1997

Related U.S. Application Data

[60] Provisional application No. 60/028,854, Oct. 22, 1996.

[51] Int. Cl.$^7$ .............................. A61K 38/00; C07K 5/00; C07K 7/00
[52] U.S. Cl. .............................. 514/12; 530/324; 530/300
[58] Field of Search ............................ 514/12; 530/324

[56] References Cited

U.S. PATENT DOCUMENTS 5,665,704   9/1997   Lowe et al. .............................. 514/12

FOREIGN PATENT DOCUMENTS

| | | |
|---|---|---|
| 341603 | 11/1989 | European Pat. Off. . |
| 356124 | 2/1990 | European Pat. Off. . |
| 385476 | 9/1990 | European Pat. Off. . |
| WO 89/10935 | 11/1989 | WIPO . |
| WO 89/12060 | 12/1989 | WIPO . |
| WO 89/12069 | 12/1989 | WIPO . |
| WO 90/01940 | 3/1990 | WIPO . |
| WO 91/09627 | 7/1991 | WIPO . |
| WO 95/13296 | 5/1995 | WIPO . |
| WO 95/28952 | 11/1995 | WIPO . |

OTHER PUBLICATIONS

Aburaya, M. et al., "Concentration and Molecular Forms of Brain Natriuretic Peptide in Rat Plasma and Spinal Cord" *Biochem. & Biophys. Res. Comm.* 177(1):40–47 (1991).

Aburaya, M. et al., "Distribution and Molecular Forms of Brain Natriuretic Peptide in Porcine Heart and Blood" *Biochem. & Biophys. Res. Comm.* 165(2):872–879 (1989).

Aburaya, M. et al., "Distribution and Molecular Forms of Brain Natriuretic Peptide in the Central Nervous System, Heart and Peripheral Tissue of Rat" *Biochem. & Biophys. Res. Comm.* 165(2):880–887 (1989).

Aburaya, M. et al., "Isolation and Identification of Rat Brain Natriuretic Peptides in Cardiac Atrium" *Biochem. & Biophys. Res. Comm.* 163(1):226–232 (1989).

Bass et al., "Hormone Phage: An Enrichment Method for Variant Proteins with Altered Binding Properties" *Proteins: Structure, Function, and Genetics* 8(4):309–314 (1990).

Bennett et al., "Extracellular Domain–IgG Fusion Proteins for Three Human Natriuretic Peptide Receptors. Hormone Pharmacology and Application to Solid Phase Screening of Synthetic Peptide Antisera" *The Journal of Biological Chemistry* 266(34):23060–23067 (Dec. 5, 1991).

Chang, M. et al., "Differential activation by atrial and brain natriuretic peptides of two different receptor guanylate cyclases" *Nature* 341:68–72 (1989).

Chinkers, M. et al., "A membrane form of guanylate cyclase is an atrial natriuretic peptide receptor" *Nature* 338:78–83 (1989).

Cunningham et al., "Production of an Atrial Natriuretic Peptide Variant that is Specific for Type A Receptor" *EMBO Journal* 13(11):2508–2515 (1994).

De Lean, A. et al., "Identification of Aldosterone Secretion Inhibitory Factor in Bovine Adrenal Medulla" *Life Sciences* 36:2375–2382 (1985).

Fethiere, J. et al., "Pharmacological Evidence for the Heterogeneity of Atrial Natriuretic Factor–$R_1$ Receptor Subtype" *Molecular Pharmacology* 40:915–922 (1991).

Flynn, T.G. et al., "Isolation and Characterization of Iso–r–ANP, A New Natriuretic Peptide from Rat Atria" *Biochem. & Biophys. Res. Comm.* 161(2):830–837 (1989).

Fuller, F. et al., "Atrial Natriuretic Peptide Clearance Receptor—Complete Sequence and Functional Expression of cDNA Clones" *The Journal of Biological Chemistry* 263(19):9395–9401 (1988).

Hanford, D.S. et al., "Brain Natriuretic Peptide is Induced by $\alpha_1$–Adrenergic Agonists as a Primary Response Gene in Cultured Rat Cardiac Myocytes" *The Journal of Biological Chemistry* 269(42):26227–26233 (1994).

Higuchi, K. et al., "Porcine Brain Natriuretic Peptide Receptor in Bovine Adrenal Cortex" *Life Sciences* 44:881–886 (1989).

Hill, N.S. et al., "Brain natriuretic peptide: possible role in the modulation of hypoxic pulmonary hypertension" *Am. J. Physiol.* 266:L308–L315 (1994).

Hirata, Y. et al., "Brain natriuretic peptide interacts with atrial natriuretic peptide receptor in cultured rat vascular smooth muscle cells" *FEBS Letters* 238(2):415–418 (1988).

Hosoda, K. et al., "Expression of Brain Natriuretic Peptide Gene in Human Heart—Production in the Ventricle" *Hypertension* 17(6):1152–1155 (1991).

Itoh, H. et al., "Occurrence of a Novel Cardiac Natriuretic Peptide in Rats" *Biochem. & Biophys. Res. Comm.* 161(2):732–739 (1989).

Jennings, D.B. et al., "The disulfide bonded ring of iso–r–ANP, unlike that of rANP, has potent cardiovascular activity" *Can. J. Physiol. Pharmacol.* 68:131–136 (1990).

Kambayashi et al., "Biological Characterization of Human Brain Natriuretic Peptide (BNP) and Rat BNP: Species–Specific Actions of BNP" *Biochem. & Biophys. Res. Comm.* 173:599–605 (1990).

Kambayashi, Y. et al., "Isolation and sequence determination of human brain natriuretic peptide in human atrium" *FEBS Letters* 259(2):341–345 (1990).

Kambayashi, Y. et al., "Isolation and Sequence Determination of Rat Cardiac Natriuretic Peptide" *Biochem. & Biophys. Res. Comm.* 163(1):233–240 (1989).

(List continued on next page.)

*Primary Examiner*—Avis M. Davenport
*Attorney, Agent, or Firm*—Jeffrey S. Kubinec

[57] ABSTRACT

Compounds related to BNP have reduced binding affinity for the natriuretic peptide receptor-C but possess improved or equivalent affinity to the wild type BNP for natriuretic peptide receptor-A. The BNP related compounds are suitable for use in the treatment or prophylaxis of various pathological conditions associated with water or electrolyte imbalance.

14 Claims, 2 Drawing Sheets

OTHER PUBLICATIONS

Kangawa, K. et al., "Purification and Complete Amino Acid Sequence of α–Human Atrial Natriuretic Polypeptide (α–hANP)" *Biochem. & Biophys. Res. comm.* 118:131–139 (1984).

Kohno, M. et al., "Pulmonary Arterial Brain Natriuretic Peptide Concentration and Cardiopulmonary Hemodynamics During Exercise in Patients with Essential Hypertension" *Metabolism* 41:1273–1275 (1992).

Kojima et al., "Cloning and sequence analysis of cDNA encoding a precursor for rat brain natriuretic peptide" *Biochem. & Biophys. Res. Comm.* 159(3):1420–1426 (1989).

Konrad, E.M. et al., "Brain natriuretic peptide binding sites in rats: in vitro autoradiographic study" *Am. J. Physiol.* 259:E246–E255 (1990).

Lowe, D.G. et al., "cDNA sequence of the human atrial natriuretic peptide clearance receptor" *Nucleic Acids Research* 18(11):3412 (1990).

Lowe, D.G. et al., "Human Natriuretic Peptide Receptor–A Guanylyl Cyclase—Hormone Cross–Linking and Antibody Reactivity Distinguish Receptor Glycoforms" *The Journal of Biological Chemistry* 267(30):21691–21697 (1992).

Lowman et al., "Selecting High–Affinity Binding Proteins by Monovalent Phage Display" *Biochemistry* 30:10832–10838 (1991).

Maack, T., "Receptors of Atrial Natriuretic Factor" *Annu. Rev. Physiol.* 54:11–27 (1992).

Maekawa, K. et al., "Cloning and Sequence Analysis of cDNA Encoding a Precursor for Porcine Brain Natriuretic Peptide" *Biochem. & Biophys. Res. Comm.* 157(1):410–416 (1988).

McGregor, A. et al., "Brain Natriuretic Peptide Administered to Man: Actions and Metabolism" *Journal of Clinical Endocrinology and Metabolism* 70(4):1103–1107 (1990).

Mimeault et al., "Evaluation of Conformational and Binding Characteristics of Various Natriuretic Peptides and Related Analogs" *Biochemistry* 34:955–964 (1995).

Mimeault, M. et al., "Development of Natriuretic Peptide Analogs Selective for the Atrial Natriuretic Factor–$R_{1A}$ Receptor Subtype" *Molecular Pharmacology* 43:775–782 (1993).

Mukoyama, M. et al., "Brain Natriuretic Peptide as a Novel Cardiac Hormone in Humans—Evidence for an Exquisite Dual Natriuretic Peptide System, Atrial Natriuretic Peptide and Brain Natriuretic Peptide" *J. Clin. Invest.* 87:1402–1412 (1991).

Mukoyama, M. et al., "Human brain natriuretic peptide, a novel cardiac hormone" *Lancet* 335:801–802 (1990).

Mukoyama, M. et al., "Increased Human Brain Natriuretic Peptide in Congestive Heart Failure" *New England J. of Medicine* 323(11):757–758 (1990).

Nakagawa, O. et al., "Rapid Transcriptional Activation and Early mRNA Turnover of Brain Natriuretic Peptide in Cardiocyte Hypertrophy—Evidence for Brain Natriuretic Peptide as an "Emergency" Cardiac Hormone against Ventricular Overload" *J. Clin. Invest.* 96:1280–1287 (1995).

Nguyen, T.T. et al., "Aldosterone Secretion Inhibitory Factor: A Novel Neuropeptide in Bovine Chromaffin Cells" *Endocrinology* 124(3):1591–1593 (1989).

Nguyen, T.T. et al., "Purification and Primary Structure of Pro–Aldosterone Secretion Inhibitory Factor from Bovine Adrenal Chromaffin Cells" *Molecular Endocrinology* 3(11):1823–1829 (1989).

Norman, J.A. et al., "Degradation of Brain Natriuretic Peptide by Neutral Endopeptidase: Species Specific Sites of Proteolysis Determined by Mass Spectrometry" *Biochem. & Biophys. Res. Comm.* 175(1):22–30 (1991).

Nutt et al., "Chemical Synthesis and Structure–Activity Relations for ANF Analogues" *Endocrinology and Metabolism Clinics of North America* 16(1):19–41 (1987).

Ogawa, Y. et al., "Molecular Cloning of the Complementary DNA and Gene That Encode Mouse Brain Natriuretic Peptide and Generation of Transgenic Mice That Overexpress the Brain Natriuretic Peptide Gene" *J. Clin. Invest.* 93:1911–1921 (1994).

Ogawa, Y. et al., "Rat Brain Natriuretic Peptide—Tissue Distribution and Molecular Form" *Endocrinology* 126(4):2225–2227 (1990).

Rosenzweig, A. et al., "Atrial Natriuretic Factor and Related Peptide Hormones" *Annu. Rev. Biochem.* 60:229–255 (1991).

Ruskoaho, H., "Atrial Natriuretic Peptide: Synthesis, Release, and Metabolism" *Pharmacol. Rev.* 44:479–602 (1992).

Saito, Y. et al., "Brain Natriuretic Peptide is a Novel Cardiac Hormone" *Biochem. & Biophys. Res. Comm.* 158(2):360–368 (1989).

Saper, C.B. et al., "Brain natriuretic peptides: differential localization of a new family of neuropeptides" *Neuroscience Letters* 96:29–34 (1989).

Scarborough, R.M. et al., "Truncated Atrial Natriuretic Peptide Analogs—Comparison Between Receptor Binding and Stimulation of Cyclic GMP Accumulation in Cultured Vascular Smooth Muscle Cells" *Journal of Biological Chemistry* 261(28):12960–12964 (1986).

Schenk, D.B. et al., "Distinct Atrial Natriuretic Factor Receptor Sites on Cultured Bovine Aortic Smooth Muscle and Endothelial Cells" *Biochem. & Biophys. Res. Comm.* 127(2):433–442 (1985).

Schoenfeld et al., "Mutations in B–type Natriuretic Peptide Mediating Receptor–A Selectivity" *FEBS Letters* 414:263–267 (1997).

Seilhamer, J.J. et al., "Human and Canine Gene Homologs of Porcine Brain Natriuretic Peptide" *Biochemical and Biophysical Research Communications* 165(2):650–658 (1989).

Shimekake, Y. et al., "The role of the C–terminal region of rat brain natriuretic peptide in receptor selectivity" *FEBS Letters* 309(2):185–189 (1992).

Spodick, D.H., "Atrial Natriuretic Peptide and Pulmonary Edema" *New England J. of Medicine* 320(10):671 (1989).

Steinhelper, M.E., "Structure, Expression, and Genomic Mapping of the Mouse Natriuretic Peptide Type–B Gene" *Circulation Research* 72(5):984–992 (1993).

Sudoh, T. et al., "Cloning and Sequence Analysis of cDNA Encloding a Precursor for Human Brain Natriuretic Peptide" *Biochemical and Biophysical Research Communications* 159(3):1427–1434 (1989).

Sudoh, T. et al., "A new natriuretic peptide in porcine brain" *Nature* 332:78–81 (1988).

Tateyama, H. et al., "Concentrations and Molecular Forms of Human Brain Natriuretic Peptide in Plasma" *Biochem. & Biophys. Res. Comm.* 185(2):760–767 (1992).

Togashi, K. et al., "Concentrations of Brain Natriuretic Peptide in Treated Congestive Heart Failure" *Clinical Chemistry* 37(5):765 (1991).

Torda, T. et al., "Brain Natriuretic Peptide Receptors in the Rat Peripheral Sympathetic Ganglia" *Biochem. & Biophys. Res. Comm.* 159(3):1032–1038 (1989).

Vanneste, Y. et al., "In Vivo Metabolism of Brain Natriuretic Peptide in the Rat Involves Endopeptidase 24.11 and Angiotensin Converting Enzyme" *Biochem. & Biophys. Res. Comm.* 173(1):265–271 (1990).

Vogt–Schaden, M. et al., "Degradation of Porcine Brain Natriuretic Peptide (pBNP–26) by Endoprotease–24.11 from Kidney Cortical Membranes" *Biochem. & Biophys. Res. Comm.* 161(3):1177–1183 (1989).

Wilcox, J.N. et al., "Differential Regional Expression of Three Natriuretic Peptide Receptor Genes within Primate Tissues" *Molecular & Cellular Biology* 11(7):3454–3462 (1991).

Yoshimura, M. et al., "Hemodynamic, Renal, and Hormonal Responses to Brain Natriuretic Peptide Infusion in Patients with Congestive Heart Failure" *Circulation* 84(4):1581–1588 (1991).

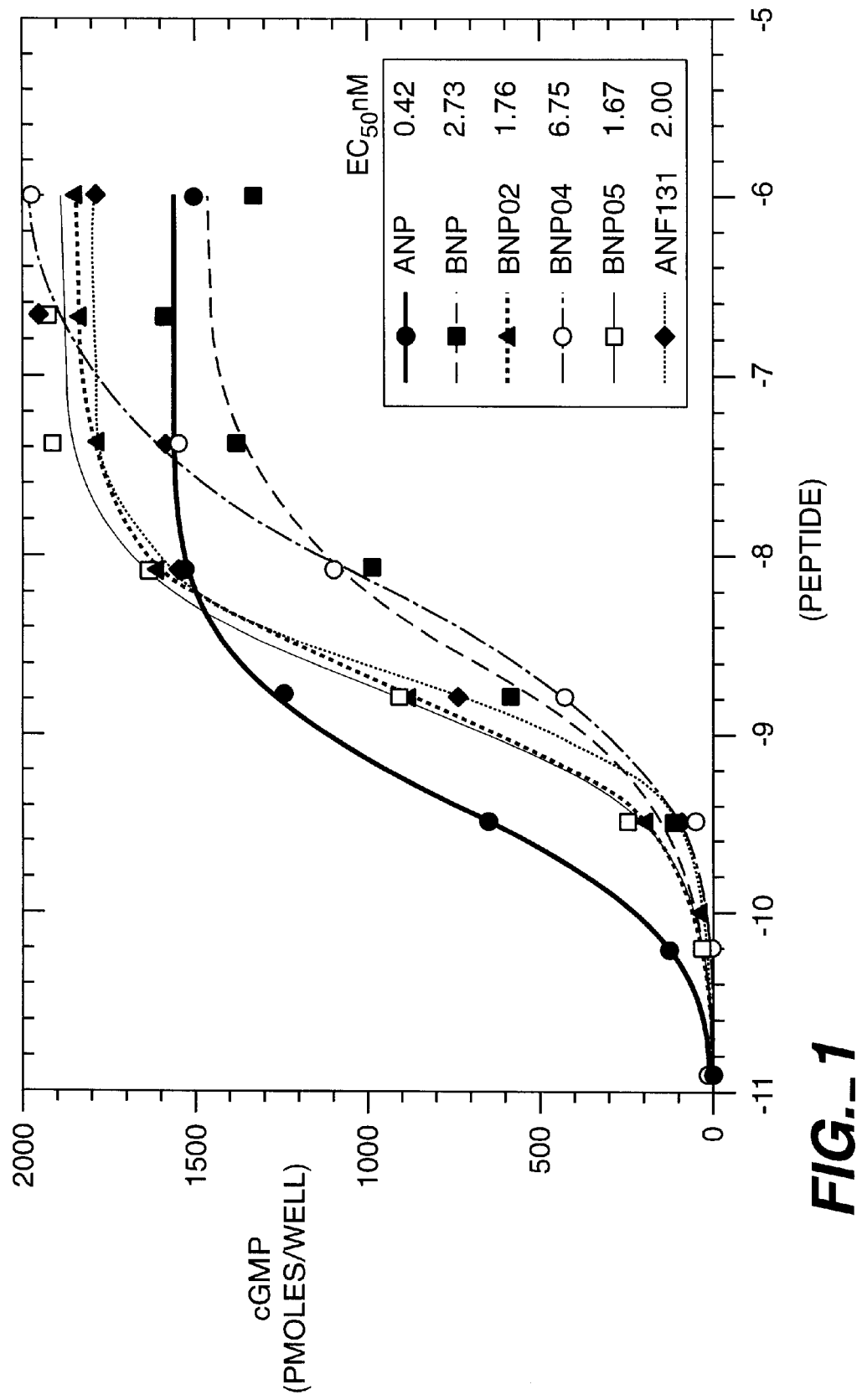
FIG._1

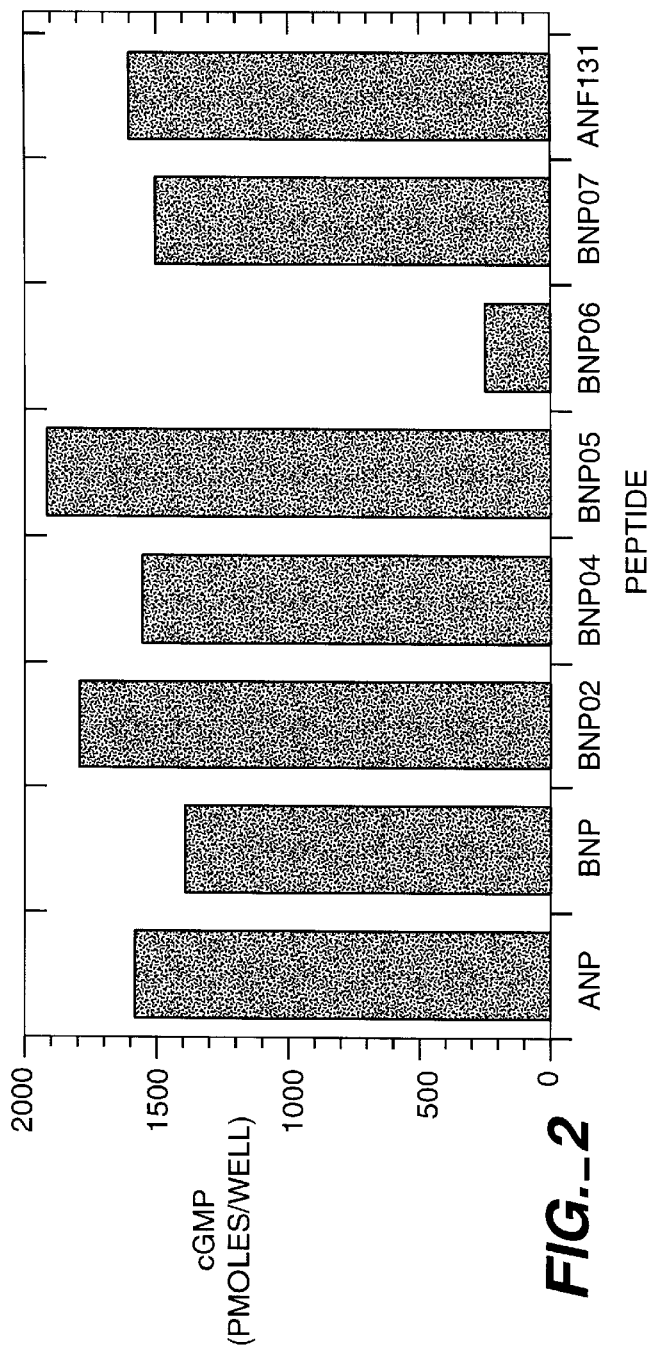

RECEPTOR SELECTIVE BNP

This application claims the benefit under 35 U.S.C. §119 of U.S. Provisional application Ser. No. 60/028,854, filed Oct. 22, 1996.

FIELD OF THE INVENTION

The present invention relates to compounds having natriuretic, diuretic, and/or vasodilatory activity in mammals. The compounds of this invention are related to B-type natriuretic peptide (BNP). In preferred embodiments the compounds exhibit decreased binding affinity to the natriuretic peptide clearance receptor (NPR-C) compared to wild-type BNP or the wild-type type A natriuretic peptide (ANP) and advantageously have enhanced potency. The invention also relates to pharmaceutical compositions comprising the novel compounds as well as their use in diagnostic, therapeutic, and prophylactic methods.

DESCRIPTION OF RELATED DISCLOSURES

Three natriuretic peptides, type A, type B and type C, have been identified which play a role in hemodynamics (Rosenzweig, A., and Seidman, C. E., (1992) Annu. Rev. Biochem. 60:229–255; Ruskoaho, H. (1992) Pharmacol. Rev. 44:479–602). The bioactive peptides are derived from prohormones each of which arises from a distinct gene (Steinhelper, M., (1993) Circ. Res. 72:984–992). The genes are expressed in a tissue specific manner (Seilhamer et al., (1989) Biochem. Biophys. Res. Commun. 165, 650–658) and are present in the systemic circulation. The type A (ANP) and type B (BNP) peptides are derived from the myocardium, whereas the type C (CNP) peptide is thought to be derived from endothelial cells. Each of the bioactive peptides, derived from the C-terminal portion of the respective prohormone, exhibit a high degree of sequence homology within their 17 amino acid ring structures.

Both ANP and BNP are primarily cardiac hormones that are released by the heart in its role as an endocrine organ regulating fluid and electrolyte hemostasis. Human BNP is stored in the atrium and ventricle (Hosodo et al., (1991) Hypertension 17:1152–1156) as the mature hormone whereas ANP is stored in cardiocytes as the precursor. BNP was first isolated from porcine brain (Sudoh et al., (1988) Nature 332:78–81) although it is synthesized in and secreted into the circulation from the porcine heart (Aburaya et al., (1989) Biochem. Biophys. Res. Commun. 158:360–368). Porcine BNP circulates as a 26 or 32 amino acid polypeptide and exhibits structural homology with ANP (Sudoh et al., (1988) Nature 332:78–81). The cDNA sequence encoding human BNP precursor, hBNP[1–108] has been determined (Sudoh, et al., (1989) Biochem. Biophys. Res. Commun. 159:1427–1434). Human BNP has also been isolated as a 32 amino acid polypeptide from human atrium the circulating form being identical to sequence residues [77–108] of the human BNP precursor molecule.

The action of the natriuretic peptides is mediated through the binding of the peptides to cellular receptors. There are at least three structurally distinct cellular receptors (Chang et al., (1989) Nature 341:68–72). NPR-A (Chinkers et al., (1090) Nature 338:78–83) and NPR-B (Lowe et al., (1990) Nucleic Acids Res. 18:3412) receptors have homologous extracellular domains of approximately 440 amino acid residues with a single transmembrane domain. Both possess intracellular guanyl cyclase and tyrosine kinase-like domains (Chang et al. (1989), supra). The extracellular domain of the third receptor NPR-C is homologous to the NPR-A and NPR-B extracellular domains but contains only a 37 amino acid intracellular domain of unknown function (Fuller et al. (1988) J. Biol. Chem. 263:9395–9401). The role of these receptors in regulating blood pressure is unclear but NPR-A is thought to be responsible for most of the biological effects of ANP and BNP (Maack T., (1992) Annu. Rev. Physiol., 54, 11–27).

BNP has peripheral and central nervous system action similar to those of ANP including natriuretic, diuretic and hypotensive effect and smooth muscle relaxation (Yoshimura et al., (1991) Circulation 84:1581–1588; Mukoyama et al., (1991) J. Clin. Invest. 87:1402–1412). Binding of the bioactive peptide to the NPR-A cellular receptor results in a number of actions including a decrease in blood pressure due in part to relaxation of vascular smooth muscle, an increase in salt and water excretion, transduction of plasma water to the interstitium and an inhibition of the release or action of aldosterone, angiotensin II, endothelin, renin and vasopressin.

Maintenance of normal extracellular fluid volume depends primarily on the excretion of sodium (natriuresis) and water (diuresis) by the kidneys. These are, in turn, primarily determined by (1) the rate at which plasma is filtered at the glomerulus (glomerular filtration rate, or GFR) and (2) the degree to which sodium is actively reabsorbed along the renal tubule (with water presumably following passively). Sodium reabsorption is regulated, in part, by the adrenal steroid hormone aldosterone, in part by blood pressure, hematocrit and plasma viscosity and in part by the various natriuretic factors or hormones (deBold, A. J. et al., (1981) Life Sciences 28:89–94; Garcia R., (1982) Experientia 38:1071–73; Currie, M. S. et al., (1983) Science 221:71–73; Flynn T. G. et al., (1983) Biochem. Biophys. Res. Commun. 117:859–865; Currie, M. G. et al., (1984) Science 223:67–69; and Kangawa, K. et al., (1984) Biochem. Biophys. Res. Commun. 118:131–139; Mukoyama et al., (1991) J. Clin. Invest. 87:1402–1412).

It is known that the serum half-life of natriuretic peptides that act as hypotensive regulators is relatively short (Crozier, I. G. et al., (1986) The Lancet II 1242–1245) and that these peptides are removed from the blood stream by several mechanisms including proteolysis and receptor mediated endocytosis by NPR-C (Maack (1992) supra). Since both ANP and BNP have a short half-life with poor or non-existent peroral absorption, synthetic analogues of BNP with longer circulatory duration and favorable in vivo characteristics are desirable.

SUMMARY OF THE INVENTION

The present invention provides compounds which have natriuretic, diuretic, and/or vasodilatory activity in mammals. The compounds of this invention are related to the B-type natriuretic peptide (BNP) and exhibit decreased binding affinity to the natriuretic peptide clearance receptor (NPR-C) compared to BNP. Advantageously, the compounds have enhanced potency defined in terms of NPR-A receptor affinity and cGMP production. In preferred embodiments, the compounds and related compositions allow for a potent NPR-A receptor stimulation providing for low dose pharmaceutical formulations. The compositions of the present invention are useful in therapeutic and prophylactic methods for inducing natruresis, diuresis or vasodilation or associated processes.

In one embodiment, the compounds of the present invention have a decreased binding affinity for the human clearance receptor (hNPR-C) compared to wild-type BNP.

Preferably, according to this aspect of the invention, the compounds exhibit the same or an increased affinity for the type-A natriuretic peptide receptor. More preferably, according to this aspect of the invention, at least one of amino acid residues Xaa19, Xaa23, Xaa24 or Xaa25 of wild-type BNP is selected according to the following scheme in order to produce a BNP variant or related compound of the invention:

Xaa19 is selected from the group consisting of Ser, Arg, Ala, Asn, Gly and conservative substitutions thereof;

Xaa23 is selected from the group Gly, Met, Phe, Leu and conservative substitutions thereof;

Xaa24 is selected from the group Trp, Tyr, Phe, and conservative substitutions thereof; and Xaa25 is selected from the group Gly, Arg, and conservative substitutions thereof.

In a further preferred embodiment, the compounds of the present invention are represented by Formula I:

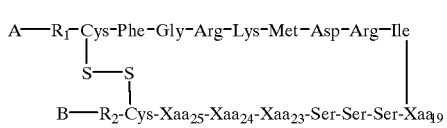

(I)

wherein:

A is selected from the group consisting of H, $C_1-C_6$ alkanoyl and Thr-Ala-Pro-Arg (SEQ ID NO:30);

$R_1$ is absent or selected from the group consisting of a peptide from between 1 and 10 amino acids, Gly-Ser-Gly-, Val-Gln-Gly-Ser-Gly (SEQ ID NO:31) and Ser-Pro-Lys-Met-Val-Gln-Gly-Ser-Gly (SEQ ID NO:32);

$Xaa_{19}$ is selected from the group consisting of Arg, Ala, Asn, Gly and Ser;

$Xaa_{23}$ is selected from the group Gly, Met, Phe, Leu;

$Xaa_{24}$ is selected from the group Trp, Tyr, Phe;

$Xaa_{25}$ is selected from the group Gly, and Arg;

$R_2$ is selected from the group consisting of a 1 to 6 amino acid peptide and Lys-Val-Leu-Arg-Arg-His- (SEQ ID NO:33); and B is selected from $OR_3$ and $NR_3R_4$ where $R_3$ and $R_4$ are independently selected from H, $C_1-C_6$alkyl, $C_6-C_{12}$aryl and $C_6-C_{12}$aryl-$C_1-C_6$alkyl.

In one embodiment, the composition of the present invention is a polypeptide and the invention encompasses a composition of matter comprising a nucleic acid, preferably DNA, encoding the polypeptide of the invention. According to this aspect, the invention further comprises an expression control sequence operably linked to the DNA molecule, an expression vector, preferably a plasmid, comprising the DNA molecule, where the control sequence is recognized by a host cell transformed with the vector, and a host cell transformed with the vector.

In one embodiment, the polypeptide compositions of the present invention may be made by a process which includes the steps of synthesizing nucleic acid sequences encoding any of the amino acid sequences of the invention, ligating the nucleic acid sequence into a suitable expression vector capable of expressing the nucleic acid sequence in a suitable host, transforming the host with the expression vector into which the nucleic acid sequence has been ligated, and culturing the host under conditions suitable for expression of the nucleic acid sequence, whereby the protein encoded by the selected nucleic acid sequence is expressed by the host. Preferably, the polypeptide is then recovered from the host cell culture. In this process, the ligating step may further contemplate ligating the nucleic acid into a suitable expression vector such that the nucleic acid is operably linked to a suitable secretory signal, whereby the amino acid sequence is secreted by the host.

The present invention further extends to therapeutic applications for the compounds described herein. Thus the invention includes a pharmaceutical composition comprising a pharmaceutically acceptable excipient and the compound of the invention. Pharmaceutical compositions comprising these compounds can be used in the treatment or prophylaxis of various pathological conditions associated with water or electrolyte imbalance and hypertension, especially renovascular hypertension. Such conditions include, for example, congestive heart failure (CHF), nephrotic syndrome and hepatic cirrhosis, pulmonary disease, and renal failure due to ineffective renal perfusion or reduced glomerular filtration rate.

BRIEF DESCRIPTION OF THE DRAWINGS

FIG. 1: Concentration responses for cGMP second messenger production on human natriuretic peptide receptor-A expressed in 293 cells. Values for the concentration of natriuretic peptide giving half-maximal stimulation of c-GMP production are given in the Figure. Values are plotted as average ± standard deviation (n=3). In the Figure ANP refers to the 28 amino acid residue peptide reported by Kangawa et al., Biochem. Biophys. Res. Comm. (1984) 118(l):131–139; BNP refers to SEQ ID NO:1; BNP02 refers to SEQ ID NO:2; BNP04 refers to SEQ ID NO:7; BNP05 refers to SEQ ID NO:7 and ANF 131 refers to SEQ ID NO:50. The results show that the peptides are full agonists on this receptor, with potency similar to BNP.

FIG. 2: Stimulation of cGMP second messenger production on human natriuretic peptide receptor-A expressed in 293 cells. cGMP values for natriuretic peptide stimulation of natriuretic peptide receptor-A at $4\times10^{-8}$M are given in the Figure. cGMP values are plotted as average ± standard deviation (n=3). In the Figure ANP refers to the 28 amino acid residue peptide reported by Kangawa et al., Biochem. Biophys. Res. Comm. (1984) 118(1):131–139; BNP refers to SEQ ID NO:1; BNP02 refers to SEQ ID NO:2; BNP04 refers to SEQ ID NO:7; BNP05 refers to SEQ ID NO:7 ANF 131 refers to SEQ ID NO:50; BNP06 refers to SEQ ID NO:48; and BNP07 refers to SEQ ID NO:49. The results show that the peptides are full agonists on this receptor, with potency similar to BNP.

FIG. 3: Alignment of the amino acid sequence of BNP from mammalian species; human (Sudoh, et al., (1989) Biochem Biophy. Res. Commun. 159:1427–1434) (SEQ ID NO:1), canine (Seilhamer et al., (1989) Biochem. Biophys. Res. Commun 165:650–658) (SEQ ID NO:44), porcine (Sudoh, T., et al., (1988) Nature 332:78–81) (SEQ ID NO:45), rat (Kojima et al., (1989) Biophys. Biochem. Res. Commun. 159:1420–1426) (SEQ ID NO:46) and mouse (Ogawa et al., (1994) J. Clin. Invest 93:1911–1921) (SEQ ID NO:47). Gaps (-) have been introduced to maximize alignment.

DETAILED DESCRIPTION OF THE PREFERRED EMBODIMENTS

Definitions

Terms used in the claims and specification are defined as set forth below unless otherwise specified.

The term amino acid or amino acid residue, as used herein, refers to naturally occurring L amino acids or to D amino acids as described further below with respect to variants. The commonly used one- and three-letter abbreviations for amino acids are used herein (Bruce Alberts et al., Molecular Biology of the Cell, Garland Publishing, Inc., New York (3d ed. 1994)).

As used herein the terms "BNP", "type-B natriuretic peptide", "wild-type BNP" and the like are used interchangeably and refer to a naturally occurring mammalian BNP or recombinant BNP. The sequence of BNP from mammalian species is known, for example, human (Sudoh, et al., (1989) Biochem Biophy. Res. Commun. 19:1427–1434) (SEQ ID NO:1), canine (Seilhamer et al., (1989) Biochem. Biophys. Res. Commun 165:650–658) (SEQ ID NO:44), porcine (Sudoh, T., et al., (1988) Nature 332:78–81) (SEQ ID NO:45) and rat (Kojima et al., (1989) Biophys. Biochem. Res. Commun. 159:1420–1426) (SEQ ID NO:46). The terms "human BNP," "HBNP" and the like, mean the 32 amino acid residue peptide reported by Sudoh, T., et al., (1989) supra having the following primary amino acid sequence:

```
1 2 3 4 5 6 7 8 9 10 11 12 13 14 15 16 Ser-Pro-Lys-Met-Val-Gln-
Gly-Ser-Gly-Cys-Phe-Gly-Arg-Lys-Met-Asp 17 18 19 20 21 22
23 24 25 26 27 28 29 30 31 32 Arg-Ile-Ser-Ser-Ser-Ser-Gly-
Leu-Gly-Cys-Lys-Val-Leu-Arg-Arg-His           (SEQ ID NO:1)
```

The integers above specific residues of this structure define the residue position number. This residue position number is used in conjunction with the three letter amino acid nomenclature to designate the residue at which a substitution is made in the BNP related compounds of this invention. Thus for example, in a BNP related compound in which arginine (Arg) replaces serine (Ser) at residue position number 19 of wild-type BNP, the nomenclature "BNP Ser19Arg" or the like is used. Multiple substitutions are designated in the same manner with a comma separating each substitution. Thus for example in a BNP related compound in which phenylalanine (Phe), tryptophan (Trp) and arginine (Arg) replace amino acids 23, 24 and 25 respectively of human BNP the nomenclature "hBNP Gly23Phe, Leu24Trp, Gly25Arg" is used.

The terms "BNP variant" and "BNP related compound" are defined as a compound having at least qualitative biological activity in common with the polypeptide of SEQ ID NO:1 and having at least one amino acid substitution as defined herein for conferring receptor specificity. Preferred amino acid substitutions are outlined in Table I of Example I. The qualitating biological activity referred to is the capacity to stimulate cyclic GMP production in cells expressing the guanylate cyclase-linked natriuretic peptide receptor NPR-A. The NPR-A receptor amino acid sequence deduced from cDNAs encoding the receptor is known (Chinkers et al., (1989) Nature 338:78–83; Lowe et al. (1989) EMBO J. 8:1377–1384). Functional expression of the NPR-A receptor cDNA in cultured mammalian cells which confers both ANP and BNP binding and guanylate cyclase activity is also known (Chinkers, et al., (1989) Nature 338:78–83). Assay systems for measurement of binding affinities for NPR receptors as well as cGMP accumulation are known (see, International Application No. PCT/US94/12591).

Additionally, in preferred embodiments, the BNP variant or BNP related compound of the present invention is believed to compete with any wild-type ANP (Kangawa et al., (1984) Biochem. Biophys. Res. Commun. 118(l): 131–139) or BNP for binding to the NPR-A receptor and thereby inducing cGMP accumulation. Therefore, without limitation to any one theory, qualitating biological activity may be defined as the ability to compete with any wild-type BNP or ANP for binding to NPR-A receptor thereby inducing cGMP accumulation. As will be appreciated from the foregoing, the term "compete" and "ability to compete" are relative terms. Thus the terms, when used to describe the activity of the BNP variant, mean a BNP variant that when added in a 10-fold molar excess to wild-type BNP or wild-type ANP in a standard receptor binding assay produces at least a 50% inhibition of binding of the wild-type BNP or wild-type ANP. Preferably the BNP variant will produce at least a 50% inhibition of binding in a 5-fold molar excess and most preferably at least a 2-fold molar excess. A most preferred BNP variant or BNP related compound of the present invention will produce at least a 50% inhibition of binding when present in a 1:1 stoichiometric ratio with wild-type BNP or wild-type ANP. For assay systems to measure binding of hBNP, hANP and the compounds of this invention to hNPR-C and hNPR-A see: Bennett et al., (1991) J. Biol. Chem. 266:23060–23067; Cunningham et al., (1994) J. EMBO 13:2508–2515; Chinkers et al., (1989) Nature 338:78–83 and Fuller et al., (1988) J. Biol. Chem. 263:9395–9401; Schank, D. B., et al., (1985) Biochem. Biophys. Res. Comm. 127:433–442; Scarborough, R. M., (1986) J. Biol. Chem. 261:12960–12964 and WO 90/01940.

A characteristic of the BNP related compound or BNP variant of the present invention is a decreased affinity for the natriuretic clearance receptor NPR-C. Therefore variants or compounds of the present invention have at least qualitative biological activity in common with wild-type BNP but have a decreased affinity for the clearance receptor NPR-C when compared to BNP in a standard receptor binding assay as described herein (see Bennett et al., (1991) J. Biol. Chem. 266:23060–23067).

The BNP variants and compounds of the present invention are, in general, homologous amino acid sequences of the rat, porcine, canine or other mammalian BNP's or homologous amino acid sequences of the sequence of SEQ ID NO:1 including homologous in vitro generated variants having the qualitative biological activity defined above. Homology with respect to the BNP variants of the present invention is defined as the percentage of amino acid residues in a candidate sequence that are identical with either the amino acid residues in SEQ ID NO:1, the amino acid sequence of a mammalian BNP or a composite sequence as defined herein after aligning the sequences and introducing gaps if necessary to achieve the maximum identity (FIG. 3). No N- or C-terminal extension or deletion in the candidate sequence shall be construed as reducing identity. "Composite amino acid" within the present invention refers to an alternate amino acid having the same position in the 32 amino acid residue structure as human BNP from other mammalian vertebrate species. Therefore, an amino acid substitution referred to as a composite amino acid substitution replaces the identified amino acid with the equivalent or composite amino acid from another mammalian species. A composite BNP sequence is defined as having at least one amino acid from the wild-type sequence replaced with a composite amino acid from another mammalian species.

Therefore, the invention contemplates a BNP variant having at least the qualitative biological activity as defined above and having, for example, at least about 75% amino acid homology with the polypeptide of SEQ ID NO:1 or the polypeptide of SEQ ID NO:1 lacking the 5 carboxyl terminal amino acid residues and/or the 9 amino terminal residues. The BNP variant amino acid sequence preferably will share at least 80%, more preferably, greater than 85% sequence homology with the sequence of SEQ ID NO:1.

However, a BNP variant or related compound may exhibit less than 50% sequence homology with the sequence of SEQ ID NO:1 and still retain the characteristics of the BNP variant or BNP related compound as defined above.

Included in the definition of BNP variant or BNP related compound of the present invention are amino acid sequence variants of the SEQ ID NO:1 wherein an amino acid in addition to those described herein which confer receptor specificity has been substituted by another residue, including predetermined mutations (e.g. site directed PCR mutagenesis); other composite amino acid substitutions from other mammalian species of BNP such as those listed above and other naturally occurring variants of the foregoing and human sequences. According to this aspect of the present invention reference is made to FIG. 3 and the amino acid sequence data presented therein. Also included is a BNP variant as described above wherein the BNP variant has been modified by substitution, chemically, enzymatically, or by other appropriate means with a moiety other than a naturally occurring amino acid, it being understood that the variant will have the qualitative biological activity described above. Exemplary non-naturally occurring amino acid substitution include those described herein below.

Additionally, amino acid sequence variants can be generated by substitutions which utilize the D rather than L form of an amino acid. This is especially useful in stabilizing the BNP variant of the present invention against enzymatic degradation. Such stabilizing amino acid substitutions have been described for ANP (Nutt and Veber, (1987) Endocrin. and Metab. Clin. N. Amer. 16(1):19–41). Such structure/activity studies of ANP analogues including the introduction of D-amino acids where appropriate can be conducted for BNP and are included in the definition of BNP variant or BNP related compound. Thus the term variant is meant to include, in addition to those substitutions described herein for receptor specificity, substitutions that confer increased stability of BNP molecules such as chiral amino acid replacements which may offer resistance to metabolic degradation. The present invention is meant to include BNP variants and related compounds that have decreased susceptibility to hydrolysis by neutral endopeptidase 24.11 (EC3.4.24.11) (NEP) and angiotensin converting enzyme (ACE) as well as improved potency or duration of action. For example, the replacement of amide bonds optionally with an amide isostere has been demonstrated for ANP. Replacements which decrease susceptibility to hydrolysis by the neutral endopeptidase 24.11 or ACE produce a BNP variant that is resistant to enzymatic degradation. Strategies include the substitution of amino acids with N-alkylated amino acids such as N-Me-Phe and addition of the urodilatin peptide tail Thr-Ala-Pro-Arg (SEQ ID NO:30).

Also included in the scope of the BNP variant and related compounds is a BNP variant wherein an amino acid has been added to or deleted from the N-terminal or C-terminal 17 member ring structure of wild-type BNP. Amino acid sequence insertions include carboxyl-terminal fusions ranging in length from one residue to polypeptides containing a hundred or more residues including pre and pro amino acid sequences as described (see for example Ogawa et al., (1994) J. Clin. Invest. 93:1911–1921). Other examples of terminal insertions include BNP variants with a composite N-terminal or C-terminal sequence from another mammalian species or from another natriuretic peptide (see FIG. 3). Such amino terminal substitutions have been described (Shimekake et al., (1992) FEBS, 309(2):185–189). Suitable N-terminal sequences are described in International Publication No WO 89/12060 and include Gly; Ser Gly; Asp/Lys/Gly-Ser-Gly; Arg/His/Gln-Asp/Lys/Gly-Ser-Gly (SEQ ID NO:34); Met/Val-Arg/His/Gln-Asp/Lys/Gly-Ser-Gly (SEQ ID NO:35); Thr/Met-Met/Val-Arg/His/Gln-Asp/Lys/Gly-Ser-Gly (SEQ ID NO:36); Lys-Thr/Met-Met-Val-Arg/His/Gln-Asp/Lys/Gly-Ser-Gly (SEQ ID NO:37); Pro-Lys-Thr/Met-Met/Val-Arg/His/Gln-Asp/Lys/Gly-Ser-Gly (SEQ ID NO:3 8); and Ser-Pro-Lys-Thr/Met-Met/Val-Arg/His/Gln-Asp/Lys/Gly-Ser-Gly (SEQ ID NO:39), and are based upon the native upstream sequence for porcine, canine or human BNP or a composite thereof.

Exemplary C-terminal insertions are described in International Publication No. 89/12069 and included (OH), NH, or NR'R" where R' and R" are independently H, lower alkyl, or Asn/Lys; Asn/Lys-Val; Asn/Lys-Val-Leu; Asn/Lys-Val-Leu-Arg (SEQ ID NO:40); Asn/Lys-Val-Leu-Arg-Arg/Lys (SEQ ID NO:41); Asn/Lys-Val-Leu-Arg-Arg/Lys-Tyr-His (SEQ ID NO:42); or the amides (NH or NR'R") thereof.

As noted, in one embodiment, amino acid substitution variants have at least one amino acid residue in addition to those described herein for conferring receptor specificity in the BNP variant molecule removed and a different residue inserted in its place. The sites for substitutional mutagenesis include sites where amino acids found in the BNP variant from various species are substantially different in terms of side chain bulk, charge and or hydrophobicity. These amino acids are substituted with the exemplary conservative substitutions as described herein below including the exemplary non-naturally occurring amino acids.

Other sites of interest are those in which particular residues of wild-type BNP and the variants obtained from various species are identical. These positions may be important for the biological activity of the BNP variant or related compound. These sites, especially those falling within a sequence of at least three other identically conserved sites, are substituted in a relatively conservative manner. Such conservative substitution are shown below under the heading of preferred conservative substitutions. If such substitutions are shown to preserve qualitative biological activity as defined herein then more substantial changes denominated below as exemplary conservative substitutions may be generated and tested for biological activity.

In this regard, it is understood that amino acids are substituted on the basis of side chain bulk, charge and/or hydrophobicity. Amino acid residues are classified into four major groups as described in, for example, International Publication No. 90/01940 the disclosure of which is hereby specifically incorporated by reference and which consists of the following groups:

Acidic: The residue has a negative charge due to loss of H ion at physiological pH and the residue is attracted by aqueous solution so as to seek the surface positions in the conformation of a peptide in which it is contained when the peptide is in aqueous solution.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/non-polar: The residues are not charged at physiological pH and the residue is repelled by aqueous solution so as to seek the inner positions in the conformation of a peptide in which it is contained when the peptide is in aqueous medium. These residues are also designated "hydrophobic residues."

Neutral/polar: The residues are not charged at physiological pH, but the residue is attracted by aqueous solution so as to seek the outer positions in the conformation of a peptide in which it is contained when the peptide is in aqueous medium.

Amino acid residues can be further classified as cyclic or noncyclic, aromatic or non aromatic with respect to their side chain groups these designations being commonplace to the skilled artisan.

| Original Residue | Exemplary Conservative Substitution | Preferred Conservative Substitution |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala, Phe | Leu |
| Leu | Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala | Leu |

Peptides synthesized by the standard solid phase synthesis techniques described here, for example, are not limited to amino acids encoded by genes for substitutions involving the amino acids. Commonly encountered amino acids which are not encoded by the genetic code, include, for example, those described in International Publication No. WO 90/01940, as well as 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu and other aliphatic amino acids; 2-aminoisobutyric acid (Aib) for Gly; cyclohexylalanine (Cha) for Val, and Leu and Ile; homoarginine (Har) for Arg and Lys; 2,3-diaminopropionic acid (Dpr) for Lys, Arg and His; N-ethylglycine (EtGly) for Gly, Pro, and Ala; N-ethylglycine (EtGly) for Gly, Pro, and Ala; N-ethylasparigine (EtAsn) for Asn, and Gln; Hydroxyllysine (Hyl) for Lys; allohydroxyllysine (AHyl) for Lys; 3-(and 4)hydroxyproline (3Hyp, 4Hyp) for Pro, Ser, and Thr; alloisoleucine (AIle) for Ile, Leu, and Val; p-amidinophenylalanine for Ala; N-methylglycine (MeGly, sarcosine) for Gly, Pro, and Ala; N-methylisoleucine (MeIle) for Ile; Norvaline (Nva) for Met and other aliphatic amino acids; Norleucine (Nle) for Met and other aliphatic amino acids; Ornithine (Orn) for Lys, Arg and His; Citrulline (Cit) and methionine sulfoxide (MSO) for Thr, Asn and Gln; N-methylphenylalanine (MePhe), trimethylphenylalanine, halo (F, Cl, Br, and I) phenylalanine, triflourylphenylalanine, for Phe.

A useful method for identification of certain residues or regions of the BNP variant for amino acid substitution other than those described herein for receptor specificity is called alanine scanning mutagenesis as described by Cunningham and Wells (1989) Science, 244:1081–1085. Here a residue or group of target residues are identified (e.g. charged residues such as Arg, Asp, His, Lys, and Glu) and replaced by a neutral or negatively charged amino acid to affect the interaction of the amino acids with the surrounding aqueous environment in or outside the cell. Those domains demonstrating functional sensitivity to the substitution then are refined by introducing further or other variations at or for the sites of substitution. Thus while the site for introducing an amino acid sequence variation is predetermined the nature of the mutation per se need not be predetermined. For example, to optimize the performance of a mutation at a given site, Ala scanning or random mutagenesis may be conducted at the target codon or region and the expressed BNP variants screened for the optimal combination of desired activity.

Phage display of protein or peptide libraries offers another methodology for the selection of BNP variants or BNP related compounds with improved affinity, altered specificity, or improved stability (Smith, G.P., (1991) Curr. Opin. Biotechnol. 2:668–673). High affinity proteins, displayed in a monovalent fashion as fusions with the M13 gene III coat protein (Clackson, T., (1994) et al.,Trends Biotechnol. 12:173–183), can be identified by cloning and sequencing the corresponding DNA packaged in the phagemid particles after a number of rounds of binding selection.

Other insertional BNP variants or BNP related compounds include the fusion to the N- or C-terminus of the BNP molecule of immunogenic polypeptides, e.g., bacterial polypeptides such as beta lactamase or an enzyme encoded by $E.$ $coli$ Trp locus or yeast protein, and C-terminal fusion with proteins having a long half-life such as immunoglobulin constant region or other immunoglobulin regions, albumin, or ferritin as described in WO 89/02922 published Apr. 6, 1989.

The term "$C_1$–$C_6$alkyl" when used to describe a BNP variant means a branched, unbranched or cyclic, saturated aliphatic hydrocarbon radical, having the number of carbon atoms specified. Representative examples of these alkyl radicals include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, cycolhexyl and the like. The terms "lower alkyl" and "$C_1$–$C_6$alkyl" are synonymous and used interchangeably. A preferred "$C_1$–$C_6$alkyl", group is methyl.

The term "$C_1$–$C_6$alkanoyl" when used to describe a BNP variant encompasses groups such as formyl, acetyl, propionyl, butyryl, isobutyryl, valeryl, isovaleryl, pivaloyl, caproyl, and the like.

The term "$C_6$–$C_{12}$aryl" when used to describe a BNP variant means a homocyclic hydrocarbon aromatic radical, whether or not fused, having the number of carbon atoms designated. Preferred aryl groups include phenyl, napthyl, biphenyl, phenanthrenyl, naphthacenyl, and the like (see e.g. Lang's Handbook of Chemistry (Dean, J. A., ed) $13^{th}$ ed. Table 7-2 [1985]).

The term "$C_6$–$C_{12}$aryl-$C_1$–$C_6$alkyl" when used to describe a BNP variant means one, two, or three aryl groups having the number of carbon atoms designated, appended to an alkyl radical having the number of carbon atoms designated including but not limited to;

benzyl, napthylmethyl, phenethyl, benzyhydryl (diphenylmethyl), florenyl, trityl, and the like. A preferred arylalkyl group is the benzyl group.

"Pharmaceutically acceptable salts" include both acid and base addition salts.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, maloneic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Receptor Specific BNP Variants and Related Compounds

The BNP variants and related compounds of this invention have at least one amino acid of wild-type BNP substituted as described herein for conferring NPR-A receptor specificity. Therefore, preferred compounds of this invention are synthetic hormone agonists of the human natriuretic peptide receptor-A (hNPR-A). This receptor is found in kidney, smooth muscle, adrenal and other tissues (Napier M. A. et al, (1984) Proc. Nat. Acad. Sci. USA, 81:5946–5950; Hori et al., (1985) Biochem. Biophys. Res. Commun. 129:773–779; Quirion et al., (1986) Proc. Natl. Acad. Sci. 83:174–175) and contains an intracellular guanyl cyclase domain. The action of hNPR-A is mediated by hydrolysis of GTP to produce the second messenger cGMP. Accordingly, preferred compounds of this invention stimulate hNPR-A to produce cGMP to at least the same extent as wild-type BNP.

The preferred compounds of this invention do not however bind to the human natriuretic peptide clearance receptor-C (hNPR-C) to the same extent as wild-type BNP. Both in vitro and in vivo systems can be used to identify the compounds of the present invention. Since binding of BNP to the NPR-A cellular receptor is presumptively a prerequisite to qualitative biological activity the BNP related compounds of the present invention are identified by screening for binding of the candidate compound to the NPR-A and NPR-C receptors. Primary screens for the compounds of the present invention therefore include vasorelaxant assays in rat and rabbit aorta tissues, relaxation of chick rectum intestinal smooth muscle tissue, natriuresis in rats, as well as the receptor specific binding assays and cGMP formation in cell culture assays described herein above and in the following Example sections.

For example, assays have been developed for the screening of BNP which evaluate the ability of the BNP to compete with a labeled native BNP for binding to intact cultured cells or membrane preparations derived from cultured cells expressing the cellular receptors. By way of example, NPR-A expressing 293 cells produced as described by Lowe and Fendly (1992) J. Biol. Chem. 267:21671–21697 may be utilized. Likewise the cDNA for NPR-C (Lowe et al., (1990) Nucleic acids Res. 18:3412) may be transfected into suitable host cells for continuous expression. These competitive displacement assays are considered commonplace for examining receptor ligand interactions.

According to a particular cellular assay, radiolabeled or florescent labeled BNP is incubated with immobilized NPR-A or NPR-C receptor-immunoglobulin chimeras in varying concentration of unlabeled candidate compound. Increasing concentrations of successful candidate compound effectively prevent binding of labeled BNP to immobilized receptor chimeras. The concentration of unlabeled peptide at which 50% maximal BNP is displaced is referred to as the EC50 and reflects the receptor binding affinity. Therefore a candidate compound with an EC50 of 100 nM displays a substantially weaker interaction with a receptor than peptide with an EC50 of 10 nM.

As noted above, BNP related compounds or variants within the present invention have a decreased binding affinity for NPR-C and corresponding NPR-A receptor specificity. Therefore, according to the present invention a BNP variant with an EC50 greater than wild type BNP for the NPR-C is said to display a weaker affinity for the NPR-C receptor and therefore a decreased affinity for the clearance receptor.

In a preferred embodiment, receptor specificity is reflected in the ratio of binding affinity of the candidate compound for NPR-A and NPR-C. A change in the ratio of binding affinity for the candidate compound to NPR-A compared to NPR-C is referred to as a change in receptor specificity. According to this aspect of the present invention, it is a characteristic of the BNP variant or BNP related compound to exhibit a decrease in the ratio of binding affinity for NPR-A compared to NPR-C as compared to wild-type BNP in the same assay. Preferred compounds and variants according to this aspect of the invention exhibit at least a 10 fold decrease in the ratio of the binding affinities compared to wild-type BNP and more preferably greater that a 100 fold decrease in the ratio.

This is preferably achieved by substituting an amino acid from wild-type BNP according to the scheme provided in Table I of Example I. Accordingly, substituting residue 19 with a basic amino acid, more preferably Arg, Har, Lys, Orn, and ρ-amidinophenyl-Ala and most preferably Arg; substituting residue 23 with a neutral, nonpolar, large, aromatic or nonaromatic amino acid, more preferably Val, Ile, Leu, Met, Phe, Trp, t-BuA, T-BuG, N-MeIle, Nle and Cha, and more preferably, Met, Phe or Leu; substituting residue 24 with an aromatic amino acid, more preferably Phe, Trp, and Tyr; and substituting residue 25 with a basic amino acid, more preferably Arg, Har, Lys, Orn, and ρ-amidinophenyl-Ala and most preferably Arg results in a BNP variant or related compound.

The above noted substitutions can occur individually or in combination. Preferred among the individual substitutions conferring receptor specificity is a BNP variant or related compound which has a substitution for amino acid residue 19 of wild-type BNP as provided in the preceding paragraph. Preferred among combination substitutions conferring receptor specificity is a BNP variant or related compound where each of amino acids 23, 24, and 25 of wild type BNP are substituted according to the scheme presented in the preceding paragraph. Such preferred combination substitutions may be accompanied by a substitution of residue 19 according to the scheme provided in the preceding paragraph.

Exemplary peptides are given below:

```
Ser-Pro-Lys-Met-Val-Gln-Gly-Ser-Gly-Cys-Phe-Gly-Arg-Lys-Met-Asp
Arg-Ile-Ser-Ser-Ser-Ser-Phe-Trp-Arg-Cys-Lys-Val-Leu-Arg-Arg-His
(SEQ ID NO: 2) or hBNP Gly23Phe, Leu24Trp, Gly25Arg;

Ser-Pro-Lys-Met-Val-Gln-Gly-Ser-Gly-Cys-Phe-Gly-Arg-Lys-Met-Asp
Arg-Ile-Ser-Ser-Ser-Ser-Met-Trp-Arg-Cys-Lys-Val-Leu-Arg-Arg-His
(SEQ ID NO: 3) or hBNP Gly23Met, Leu24Trp, Gly25Arg;

Ser-Pro-Lys-Met-Val-Gln-Gly-Ser-Gly-Cys-Phe-Gly-Arg-Lys-Met-Asp
Arg-Ile-Arg-Ser-Ser-Ser-Gly-Leu-Gly-Cys-Lys-Val-Leu-Arg-Arg-His
(SEQ ID NO: 4) or hBNP Ser19Arg;

Ser-Pro-Lys-Met-Val-Gln-Gly-Ser-Gly-Cys-Phe-Gly-Arg-Lys-Met-Asp
Arg-Ile-Arg-His-Ser-Ser-Gly-Leu-Gly-Cys-Lys-Val-Leu-Arg-Arg-His
(SEQ ID NO: 5) or hBNP Ser19Arg, Ser20His;

Ser-Pro-Lys-Met-Val-Gln-Gly-Ser-Gly-Cys-Phe-Gly-Arg-Lys-Met-Asp
Arg-Ile-Arg-His-Leu-Ser-Gly-Leu-Gly-Cys-Lys-Val-Leu-Arg-Arg-His
(SEQ ID NO: 6) or hBNP Ser19Arg, Ser20His, Ser21Leu;

Ser-Pro-Lys-Met-Val-Gln-Gly-Ser-Gly-Cys-Phe-Gly-Arg-Lys-Met-Asp
Arg-Ile-Arg-Ser-Ser-Ser-Phe-Trp-Arg-Cys-Lys-Val-Leu-Arg-Arg-His
(SEQ ID NO: 7) hBNP Ser19Arg Gly23Phe, Leu24Trp, Gly25Arg;

Ser-Pro-Lys-Met-Val-Gln-Gly-Ser-Gly-Cys-Phe-Gly-Arg-Lys-Met-Asp
Arg-Ile-Arg-Ser-Ser-Ser-Met-Trp-Arg-Cys-Lys-Val-Leu-Arg-Arg-His
(SEQ ID NO: 8) or hBNP Ser19Arg, Gly23Met, Leu24Trp, Gly25Arg;

Ser-Pro-Lys-Met-Val-Gln-Gly-Ser-Gly-Cys-Phe-Gly-Arg-Lys-Met-Asp
Arg-Ile-Arg-His-Ser-Ser-Met-Trp-Arg-Cys-Lys-Val-Leu-Arg-Arg-His
(SEQ ID NO: 9) or hBNP Ser19Arg, Ser20His, Gly23Met, Leu24Trp,
Gly25Arg; and Ser-Pro-Lys-Met-Val-Gln-Gly-Ser-Gly-Cys-Phe-Gly-Arg-Lys-Met-Asp
Arg-Ile-Arg-His-Leu-Ser-Met-Trp-Arg-Cys-Lys-Val-Leu-Arg-Arg-His
(SEQ ID NO: 10) or hBNP Ser19Arg, Ser20His, Ser21Leu, Gly23Met,
Leu24Trp, Gly25Arg.
```

Further compounds within the scope of the present invention are:

| | |
|---|---|
| hBNP Arg13Ser, Lys14Pro, Ser19Arg; | (SEQ ID NO: 11) |
| hBNP Lys14Thr, Ser19Arg, Ser21Gln; | (SEQ ID NO: 12) |
| hBNP Lys14Asn, Ser19Arg, Ser20His, Ser21Leu; | (SEQ ID NO: 13) |
| hBNP Lys14Asn, Ser19Ala, Ser20Arg, Ser21Glu; | (SEQ ID NO: 14) |
| hBNP Lys14Asn, Ser19Arg, Ser20Lys, Ser21Thr; | (SEQ ID NO: 15) |
| hBNP Lys14Asn, Ser19Arg, Ser20Gly; | (SEQ ID NO: 16) |
| hBNP Lys14Asn, Ser19Gly, Ser20Arg, Ser21Ala; | (SEQ ID NO: 17) |
| hBNP Lys14Asn, Ser19Arg, Ser21Trp; | (SEQ ID NO: 18) |
| hBNP Lys14Asn, Ser19Arg, Ser20Asn, Ser21Thr; | (SEQ ID NO: 19) |
| hBNP Lys14Gln, Ser19Arg, Ser20His, Ser22Thr; | (SEQ ID NO: 20) |
| hBNP Lys14Asn, Ser19Gly, Ser20His, Ser21Leu; | (SEQ ID NO: 21) |
| hBNP Lys14Asn, Ser19Arg, Ser20Thr, Ser21Lys; | (SEQ ID NO: 22) |
| hBNP Lys14Asn, Ser19Gly, Ser20Gly, Ser21Leu; | (SEQ ID NO: 23) |
| hBNP Lys14Asn, Ser19Arg; | (SEQ ID NO: 24) |
| hBNP Lys14Thr, Ser19Arg, Ser20His, Ser21Gly, Ser22Gly; | (SEQ ID NO: 25) |
| hBNP Lys14Asn, Ser19Arg, Ser20Gly, Ser21Met; | (SEQ ID NO: 26) |
| hBNP Gly23Met, Leu24Tyr, Gly25Arg; | (SEQ ID NO: 27) |

-continued hBNP Gly23Leu, Leu24Trp, Gly25Arg;    (SEQ ID NO: 28)
                                      and hBNP Gly23Met, Leu24Phe, Gly25Arg     (SEQ ID NO: 29).

Chemical Synthesis

One method of producing compounds of the present invention involves chemical synthesis of the polypeptide, followed by treatment under oxidizing conditions appropriate to obtain the native conformation, that is, the correct disulfide bond linkages. This can be accomplished using methodologies well known to those skilled in the art (see Atherton, E., and Sheppard R. C., Solid Phase Peptide Synthesis: A Practical Approach, IRL Press, Oxford England (1989); Kelley, R. F. & Winkler, M. E. in *Genetic Engineering Principles and Methods,* Setlow, J. K., ed., Plenum Press, N.Y., vol. 12, pp 1–19 (1990); Stewart, J. M. & Young, J. D. Solid Phase Peptide Synthesis, Pierce Chemical Co. Rockford, Ill. (1984)).

Polypeptides of the invention may be conveniently prepared using solid phase peptide synthesis (Merrifield, (1964) J. Am. Chem. Soc., 85:2149; Houghten, (1985) Proc. Natl. Acad. Sci. USA 82:5132). Solid phase synthesis begins at the carboxy-terminus of the putative peptide by coupling a protected amino acid to a suitable resin (e.g. chloromethylated polystyrene resin) as shown in FIGS. 1-1 and 1-2, on pages 2 and 4 of Stewart and Young supra. After removal of the α-amino protecting group with, for example, trifluoroacetic acid (TFA) in methylene chloride and neutralizing in, for example TEA, the next α-amino- and side-chain protected amino acid in the synthesis is added. The remaining α-amino- and, if necessary, side-chain-protected amino acids are then coupled sequentially in the desired order by condensation to obtain an intermediate compound connected to the resin. Alternatively, some amino acids may be coupled to one another forming a peptide prior to addition of the peptide to the growing solid phase polypeptide chain.

The condensation between two amino acids, or an amino acid and a peptide, or a peptide and a peptide can be carried out according to the usual condensation methods such as the azide method, mixed acid anhydride method, DCC (N,N'-dicyclohexylcarbodiimide) or DIC (N,N'-diisopropylcarbodiimide)methods, active ester method (p-nitrophenyl ester method, BOP [benzotriazole-1-yl-oxy-tris (dimethylamino) phosphonium hexafluorophosphate] method, N-hydroxysuccinic acid imido ester method, etc, and Woodward reagent K method.

Common to chemical synthesis of peptides is the protection of any reactive side-chain groups of the amino acids with suitable protecting groups. Ultimately these protecting groups are removed after the desired polypeptide chain has been sequentially assembled. Also common is the protection of the α-amino group on an amino acid or a fragment while that entity reacts at the carboxyl group followed by the selective removal of the α-amino-protecting group to allow subsequent reaction to take place at that location. Accordingly, it is common in polypeptide synthesis that an intermediate compound is produced which contains each of the amino acid residues located in the desired sequence in the peptide chain with various of these residues having side-chain protecting groups attached. These protecting groups are then commonly removed substantially at the same time so as to produce the desired resultant product following removal from the resin.

Suitable protective groups for protecting the α-and ε-amino side chain groups are exemplified by benzyloxycarbonyl (abbreviated Z), isonicotinyloxycarbonyl (iNOC), O-chlorobenzyloxycarbonyl [Z(2Cl)], p-nitrobenzyloxycarbonyl [Z(NO$_2$)], p-methoxybenzyloxycarbonyl [Z(OMe)], t-butoxycarbonyl, (Boc), t-amyloxycarbonyl (Aoc), isoboronyloxycarbonyl, adamatyloxycarbonyl, 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthalyl, formyl, 2-nitrophenylsulphenyl (NPS), diphenylphosphinothioyl (Ppt), dimethylophosphinothioyl (Mpt) and the like.

Protective groups for the carboxy functional group are exemplified by; benzyl ester (OBzl), cyclohexyl ester (Chx), 4-nitrobenzyl ester (ONb), t-butyl ester (Obut), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenysulfonyl (Mts), and the like. The thiol group of cysteine may be protected with p-methoxybenzyl, triphenylmethyl, acetylaminomethyl ethylcarbamoyle, 4-methylbenzyl, 2, 4, 6-trimethy-benzyl (Tmb) etc, and the hydroxyl group of serine can be protected with benzyl, t-butyl, acetyl, tetrahydropyranyl and the like.

Stewart and Young supra provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151.

After the desired amino acid sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the protein sequence is washed with ether, transferred to a large volume of dilute acetic acid, and stirred at pH adjusted to about 8.0 with ammonium hydroxide.

Preferably in order to avoid alkylation of residues in the polypeptide, (for example, alkylation of methionine, cysteine, and tyrosine residues) a thio-cresol and cresol scavenger mixture is used. The resin is washed with ether, and immediately transferred to a large volume of dilute acetic acid to solubilize and minimize intermolecular cross-linking. A 250 μM polypeptide concentration is diluted in about 2 liters of 0.1M acetic acid solution. The solution is then stirred and its pH adjusted to about 8.0 using ammonium hydroxide. Upon pH adjustment, the polypeptide takes its desired conformational arrangement.

Non-peptide (amide isostere) Linkages

In one embodiment of the invention, the amide linkages of BNP (—C(=O)—NH—) may be replaced with amide isostere linkages such as; —CH$_2$—NH—, —CH$_2$—S—, —CH$_2$—O—, —CH$_2$-CH$_2$—, —CH=CH— (cis and trans), —C(=O)—CH$_2$—, —CH(OH)—CH$_2$—, —CH(CN)—NH—, —O—C(=O)—NH— and —CH$_2$—SO—, by methods known in the art. The following references describe preparation of peptide analogs which include these alternative-linking moieties: Spatola, A. F., Vega Data 1(3): "Peptide Backbone Modifications" (General Review) (Mar. 1983), Spatola, A. F., in "Chemistry and Biochemistry of Amino Acids Peptides and Proteins", B. Weinstein, ed., Marcel Dekker, New York, p. 267 (1983); Hudson, D. et al. Int. J. Pept. Prot. Res. 14:177–185 (1979) (—CH$_2$NH—, —CH$_2$CH$_2$—); Tourwe, D., et al., Structural Biology 331–333 (1989) (E, —CH=CH—); Spatola, A. F., et al., Life Sci. 38:1243–1249 (1986) (—CH$_2$—S—); Almquist, R. G., et al., J. Med. Chem. 23:1392–1398 (1980) (—C(=O)—CH$_2$—); Jennings-White C., et al., Tetrahedron Lett 23: (1982) (—C(=O)—CH$_2$—); Szelke, M., et al., EP Application No.45655 (—CH(OH)—CH$_2$) Holladay, M. W., et al., Tetrahedron Lett 24:4401–4404 (1983) (—C(OH)—CH$_2$—); Hruby, V. J. Life Sci 31:189–199 (1982) (—CH$_2$S—); and Cho, C. Y. et al, Science 261:1303–1305 (1993)(—O—C(=O)—NH—).

Recombinant Synthesis

In a further embodiment, the present invention encompasses a nucleic acid, preferably DNA, encoding the protein component of a BNP variant that contain the amino acid substitutions described herein. The invention further comprises an expression control sequence operably linked to the DNA molecule, an expression vector, preferably a plasmid, comprising the DNA molecule, where the control sequence is recognized by a host cell transformed with the vector.

The compounds of the present invention may be made by a process which includes the steps of synthesizing (by art standard techniques) nucleic acid sequences encoding any of the amino acid sequences described herein, ligating the nucleic acid sequence into a suitable expression vector capable of expressing the nucleic acid sequence in a suitable host, transforming the host with the expression vector into which the nucleic acid sequence has been ligated, culturing the host under conditions suitable for expression of the nucleic acid sequence, whereby the protein encoded by the selected nucleic acid sequence is expressed by the host. In this process, the ligating step may further contemplate ligating the nucleic acid into a suitable expression vector such that the nucleic acid is operably linked to a suitable secretory signal, whereby the amino acid sequence is secreted by the host. The secretory signal may be selected, for example, from the group consisting of the leader sequence of stII, ecotin, lamB, herpes gD, lpp, alkaline phosphatase, invertase, and alpha factor and is preferably stII.

By way of illustration, with expression vectors encoding wild-type BNP in hand, site specific mutagenesis (Kunkel et al., Methods Enzymol. 204:125–139 [1991]; Carter, P., et al., Nucl. Acids. Res. 13:4331 [1986]; Zoller, M. J. et al.,Nucl. Acids Res. 10:6487 [1982]), cassette mutagenesis (Wells, J. A., et al., Gene 34:315 [1985]), restriction selection mutagenesis (Wells, J. A., et al., Philos. Trans, R. Soc. London SerA 317, 415 [1986]) or other known techniques may be performed on the BNP DNA. The mutant DNA can then be used in place of the parent DNA by insertion into the aforementioned expression vectors. Growth of host bacteria containing the expression vectors with the mutant DNA allows the production of mutant BNP, which can be isolated as described herein.

The host cell may be prokaryotic or eukaryotic. Prokaryotes are preferred for cloning and expressing DNA sequences to produce parent polypeptides, segment substituted polypeptides, residue-substituted polypeptides and polypeptide variants. For example, E. coli K12 strain 294 (ATCC No. 31446) may be used as E. coli B, E. coli X1776 (ATCC No. 31537), and E. coli c600 and c600hfl, E. coli W3110 (F-, gamma-, prototrophic/ATCC No. 27325), bacilli such as Bacillus subtilis, and other enterobacteriaceae such as Salmonella typhimurium or Serratia marcesans, and various pseudomonas species. The preferred prokaryote is E. coli W3110 (ATCC 27325). When expressed by prokaryotes the polypeptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure (*Tissue Culture*, Academic Press, Kruse and Patterson, editors (1973)). Examples of such useful host cell lines are VERO and HeLa cells, Chinese Hamster Ovary (CHO) cell lines, W138, 293, BHK, COS-7 and MDCK cell lines.

Preferred expression vectors of the present invention may be selected from, for example, pBR322, phGH1, pBO475, pB1537, pRIT5, pRIT2T, pKK233-2, pDR540, pPL-lambda and pB1537, with the most preferred vector being pB1537.

A preferred vector for direct expression of the BNP variants of the present invention is pB1537 (Cunningham et al. (1994) EMBO J. 13:2508–2515) and contains origins of replication for E. coli, the alkaline phosphatase promoter, the stII signal sequence, the BNP variant gene, and the ampicillin resistance gene. Other preferred vectors are pR1T5 and pR1T2T (Pharmacia Biotechnology). These vectors contain appropriate promoters followed by the Z domain of protein A, allowing genes inserted into the vectors to be expressed as fusion proteins.

Other preferred vectors can be constructed using standard techniques by combining the relevant traits of the vectors described herein. In this instance a vector containing the origins of replication for phage and E. coli, which allow it to be shuttled between such hosts, is used thereby facilitating both mutagenesis and expression (Cunningham, B., et al., Science 243:1330–1336 [1989]; Wells, J. & Cunningham, B., WO 90/04788 published May 3, 1990). Relevant traits of the vector include the promoter, the ribosome binding site, the variant gene or gene fusion (the Z domain of protein A and a BNP variant and its linker), the signal sequence, the antibiotic resistance markers, the copy number, and the appropriate origins of replication.

Gene Fusions

A variation on the above procedures contemplates the use of gene fusions, wherein the gene encoding a BNP variant is associated, in the vector, with a gene encoding another protein or a fragment of another protein. This results in a BNP variants being produced by the host cell as a fusion with another protein. The "other" protein is often a protein or peptide which can be secreted by the cell, making it possible to isolate and purify the desired protein from the culture medium and eliminating the necessity of destroying the host cells which arises when the desired protein remains inside the cell. Alternatively, the fusion protein can be expressed intracellularly. It is useful to use fusion proteins that are highly expressed.

The use of gene fusions, though not essential, can facilitate the expression of heterologous proteins in E. coli as well as the subsequent purification of those gene products (Harris, T. J. R. in Genetic Engineering, Williamson, R., Ed., Academic, London, Vol. 4, p. 127 [1983]; Uhlen, M. & Moks, T., Methods Enzymol. 185:129–143 [1990]). Protein A fusions are often used because the binding of protein A, or more specifically the Z domain of protein A, to IgG provides an "affinity handle" for the purification of the fused protein (Nilsson, B. & Abrahmsen, L. Methods Enzymol. 185:144–161 [1990]). It has also been shown that many heterologous proteins are degraded when expressed directly in E. coli, but are stable when expressed as fusion proteins (Marston, F. A. O., Biochem J. 240:1 [1986]).

BNP variants expressed as fusion proteins may be properly folded or may require folding to obtain the native structure. The properly folded fusion protein may be active and useful as pharmaceutical drug. When denaturing and refolding are needed, typically the protein is treated with a chaotrope, such a guanidine HCl, and is then treated with a redox buffer, containing, for example, reduced and oxidized dithiothreitol or glutathione at the appropriate ratios, pH, and temperature, such that the protein of interest is refolded to its native structure.

More preferred would be the correctly folded native protein that is obtained from the fusion protein by methods known in the art. Fusion proteins can be cleaved using chemicals, such as cyanogen bromide, which cleaves at a methionine, or hydroxylamine, which cleaves between an Asn and Gly. Using standard recombinant DNA methodology, the nucleotide base pairs encoding these amino acids may be inserted just prior to the 5' end of the BNP variant gene.

Alternatively, one can employ proteolytic cleavage of fusion proteins, which has been recently reviewed (Carter, P. (1990) in Protein Purification: From Molecular Mechanisms to Large-Scale Processes, Ladisch, M. R., Willson, R. C., Painton, C. C., and Builder, S. E., eds., American Chemical Society Symposium Series No. 427, Ch 13, 181–193).

Proteases such Factor Xa, thrombin, subtilisin and mutants thereof, have been successfully used to cleave fusion proteins. Typically, a peptide linker that is amenable to cleavage by the protease used is inserted between the "other" protein (e.g. the Z domain of protein A) and the protein of interest, such as a BNP variant. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

Purification and Characterization

Purification and characterization of BNP variants may be carried out by any art standard technique. For example, BNP variants may be purified from the broths of E. coli cultures grown in 10 liter fermentors by batch reverse phase chromatography, cation exchange chromatography and C18 reverse phase HPLC.

Utility and Administration

Compounds of the present invention have natriuretic, diuretic and vasorelaxant activity and may inhibit the release of aldosterone and renin. Thus, these compounds find use as therapeutic agents in the treatment of various pathological conditions associated with water or electrolyte imbalance and hypertension, especially renovascular hypertension. The compounds of the present invention can be used analogous to ANP peptides in therapeutic and prophylactic measures. BNP has potent diuretic and systemic vasorelaxant properties (Kambayashi et al., (1990) Biochem. Biophys. Res. Commun. 173:599–605). Increased levels of BNP have been reported in congestive heart failure and during acute exercise (Kohno, M., et al., (1992) Metabolism 41:1273–1275; Mukoyama M., et al., (1991) J. Clin. Invest. 87:1402–1412). Both BNP and ANP are unregulated proportionally during chronic hypoxia (Am. J. Physiol. (1994) 266:L308–L315). Therefore any condition resulting in blood volume or blood pressure overload is a candidate. Such conditions include, for example, cardiac diseases such as congestive heart failure (CHF), cardiomyopathies, myocarditis, valve diseases such as rheumatic heart disease, coronary heart disease such as myocardial ischemia and infarction, arrhythmias such as paroxysmal atrial tachycardia and atrial fibrillation and flutter, congenital heart defects, restrictive disorders such as pericarditis and cardiac tamponade, drug induced cardiac diseases, hypertension, including essential hypertension, secondary, pulmonary and portal hypertension, kidney diseases such as chronic renal failure and nephrosis, cirrhosis, primary aldosteronism, Cushing's disease, preeclampsia, toxemia of pregnancy, premenstrual syndrome, nephrotic syndrome and hepatic cirrhosis, pulmonary disease, and renal failure due to ineffective renal perfusion or reduced glomerular filtration rate.

The compounds and compositions can be administered to humans in a manner similar to ANP and other similar therapeutic agents. The dosage to be administered will depend on the usual factors including; age, weight, sex, condition of the patient, specific disorder being treated, and route of administration. In general, the dosage required for therapeutic efficacy will range from about 0.01 to 1000 mg/kg, more usually 0.1 to 25 mg/kg of the host body weight. Alternatively, dosages within these ranges can be administered by constant infusion over an extended period of time until the desired therapeutic benefits have been obtained.

The present invention also provides compositions containing an effective amount of compounds of the present invention, including the nontoxic addition salts, amides and esters thereof, which may, alone, serve to provide the above-recited therapeutic benefits. The peptide compounds may be formulated into the compositions as neutral or salt forms. Pharmaceutically acceptable nontoxic salts include the acid addition salts (formed with the free amino groups) and which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropyl amine, 2-ethylamino ethanol, histidine, procaine, and the like. Such compositions can be provided together with physiologically tolerable liquid, gel or solid diluents, adjuvants and excipients.

Typically, such compositions are prepared as sterile, injectable liquid solutions or suspensions. Compositions may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like. For a more detailed description of the foregoing see a standard pharmaceutical text such as *Remington's Pharmaceutical Sciences,* Mack Publishing Co. Easton, Pa. (1970).

In addition to the compounds of the present invention which display natriuretic, diuretic or vasorelaxant activity, compounds of the present invention can also be employed as intermediates in the synthesis of such useful compounds. Alternatively, by appropriate selection, compounds of the present invention whose activity levels are reduced or eliminated entirely can serve to modulate the activity of other diuretic, natriuretic or vasorelaxant compounds, including compounds outside the scope of the present invention, by, for example, binding to alternate receptors, stimulating receptor turnover, or providing alternate substrates for degradative enzyme of receptor activity and thus inhibiting these enzymes or receptors. When employed in this manner, such compounds can be delivered as admixtures with other active compounds or can be delivered separately, for example, in their own carriers.

Pharmaceutical compositions may be prepared alone or in combination with a C receptor ligand such as, for example SC-46542, or an inhibitor of the enzyme primarily responsible for the degradation of BNP such as SCH 32615, SCH 344826, SCH 39370, SQ 2900072, thiorfan and UK 69578. Sythetic compounds which occupy the C-receptor increase the concentrations of circulating BNP and may be used in combination with the peptides of the present invention. U.S. Pat. No. 4,740,499 describes a method of prolonging or enhancing the bioactivity of an atrial peptide using two specific inhibitor of endopeptidase 24.11, thiorphan or kelotorphan administered simultaneously with the atrial peptides.

The following examples are offered by way of illustration and not by way of limitation. The disclosures of all citations in the specification are expressly incorporated herein by reference.

EXAMPLES

Example I

Monovalent phage display (Bass et al., (1990) Protein Struct. Funct. Genent., 8:309–314; Lowman et al., (1991) Biochemistry, 30:10832–10838) was used to screen variants of BNP for ones that bind tightly to human NPR-A and not to NPR-C. After multiple enrichment screen BNP variants that bound preferentially to NPR-A were isolated.

Construction of Libraries: Monovalent phagemid libraries (Lowman, H. B. et al., (1991) Methods: Companion Methods Enzymol. 3:205–216) of BNP were generated by site directed mutagenesis (Kunkel, T. A., et al., (1991) Methods Enzymol. 204:125–139). Each library contained three, four or five codons fully randomized for all 20 amino acids (as shown in Table 1 below) using oligonucleotides that mutated target codons to NNS sequences (where N represents a mixture of all four bases and S is a mixture of both C and G). Stocks of approximately $10^{14}$ phagemid per mL were prepared from PEG precipitates of culture broths from XL-1 Blue cells containing the plasmid and superinfected with KO7 helper phage.

Selection of receptor specific BNP variants: Before negatively selecting for NPR-A specific mutants the libraries were pre-enriched for NPR-A binders using NPR-A IgG fusion (A-IgG) (Bennett et al. (1991) J. Biol. Chem. 266:23060–23067). Wells of Maxisorb microtiter plates (Nunc cat. #439454) were coated with 100 μl of 2 μg/ml Rabbit anti-human $F_c$ Antibody (Jackson Immuno Research cat. #309–006–008) in 50 mM sodium bicarbonate (pH 9.6) at 4° C. overnight. The coat solution was discarded and the wells were blocked for one hour at room temperature with 5% skim milk in 25 mM sodium carbonate (pH9.6). After washing with 0.01% Tween® in PBS, NPR-A IgG was added at 1 μg/ml in binding buffer (2% skim milk in PBS) for 1 hour at room temperature. The wells were washed again. 10 μl of phage stock (250 fold concentrated from growth media, stored in PBS) was brought up to 100 μl with binding buffer and incubated in the wells for 2 hours at room temperature. After washing 20–30 times, the phage were eluted with 100 μl 0.2M glycine (pH 2.0), then neutralized with 13 μl 1M Tris Base and titered by infecting E. coli (XL1-blue Stratagene, Inc., San Diego, Calif.). The remaining selected phagemid particles were propagated for the use in the next selection cycle. Receptor specific selection was done by adding competing NPRC IgG (Bennett et al. (1991) supra) during the phage binding step in the NPR-A IgG coated wells. This was done in seven rounds of selection with the amount of competing CIgG increasing from 20 nM to 200 nM. For each library, there were control wells that lacked either the competing CIgG or both the AIgG coat and the CIgG.

ELISA measurement of phagemic affinities for NPR-A and NPR-C: Phage ELISA were determined according to the method of Cunningham, B. C. et al., (1994) EMBO J., 13:2508–2515. Microtiter plates (Nunc, Maxisorb, 96 wells) were coated with purified A-IgG (at 1 μg/ml) in 50 mM sodium bicarbonate (pH 9.6) at 4 C overnight. The plates were blocked with 5% skimmed milk and washed with PBS, 0.01% TWEEN 20. Serial dilutions of competing receptor (A-IgG or C-IgG) and a subsaturating concentration of BNP-phagemid were added to wells in 100 μl of binding buffer (2% skim milk in PBS). After 2 h the plates were washed, and the bound phagemid stained with sheep anti-M13 HRP conjugate antibody (Pharmacia #279402-01), and assayed. Affinities (EC50) were calculated as the concentration of competing receptor that resulted in half-maximal phagemid binding.

Results

The amino acid residues found at each randomized position after 7 rounds of selection are shown in Table I. 8 segments of 3 to 5 amino acids randomized by primer mutagenisis are indicated at the top of the figure, immediately above the numbering for 32 amino acid human BNP, the sequence of which is shown in single letter amino acid code. Cysteine residues 10 and 26 were not mutagenized since they form a disulfide bond essential for binding to NPR-A. The substitution of K3 for D (Display BNP) is analogous to the acidic substitution R3D in ANP used to facilitate secretion expression in E. coli (Cunningham et al. (1994)). Individual clones were picked and the DNA sequence was determined. The number of times a particular sequence was observed is shown on the left. The ratio of mutant BNP phagemid binding affinity to ANP phagemid binding to A-IgG is shown on the right. Mutations that occur outside of the mutagenesis window result from polymerase misincorporation mutations that render a selection advantage to the mutant BNP phagemid (Cunningham et al. (1994)).

TABLE I

| | 1 | | | | | 2 | | | | 3 | | | | 4 | | | | 5 | | | | 6 | | | 7 | | | 8 | | Binding to NPR-A |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | ratio of |
| Human BNP | S | P | K | M | V | Q | G | S | G | C | F | G | R | K | M | D | R | I | S | S | S | S | G | L | G | C | K | V | L | R | R | H | mutant/hANP |
| Display BNP | | | D | | | | | | | | | | | | | | | | | | | | | | | | | | | | | | |
| # of clones found | | | | | | | | | | | | | | | | | | | | | | | | | | | | | | | | | |
| [2] | E | V | E | E | M | | | | | | | | | | | | | | | | | | | | | | | | | | | | |
| [1] | D | E | Q | L | E | | | | | | | | | | | | | | | | | | | | | | | | | | | | |
| [1] | S | E | D | Y | E | | | | | | | | | | | | | | | | | | | | | | | | | | | | |
| [1] | N | W | D | D | M | | | | | | | | | | | | | | | | | | | | | | | | | | | | |
| [2] | | | | | | N | E | E | S | | | | | | | | | | | | | | | | | | | | | | | | 80.0 |
| [1] | | | | | | M | R | D | E | | | | | | | | | | | | | | | | | | | | | | | | 5.5 |
| [1] | | | | | | M | R | D | E | | | | | | | | | | | | | | | | | | | | | | | | |
| [6] | | | | | | | | | | | | | S | P | | | | | | | | | | | | | | | | | | | 1.6** |
| [5] | | | | | | | | | | | | R | G | R | | | | | | | | | | | | | | | | | | | SRB |
| [3] | | | | | | | | | | | | | G | L | | | | | | | | | | | | | | | | | | | 26.2 |
| [1] | | | | | | | | | | | G | P | N | R | | | | | | | | | | | | | | | | | | | |
| [9] | | | | | | | | | | | | | | N | | | | | R | | | | | | | | | | | | | | 14.2 |
| [12] | | | | | | | | | | | | | | T | | | | | R | A | E | | | | | | | | | | | | 4.2 |
| [10] | | | | | | | | | | | | | | N | | | | | R | S | Q | | | | | | | | | | | | 1.0** |
| [1] | | | | | | | | | | | | | | N | | | | | A | H | L | | | | | | | | | | | | 1.3 |
| [1] | | | | | | | | | | | | | | N | | | | | N | R | E | | | | | | | | | | | | 4.2 |
| [3] | | | | | | | | | | | | | | N | | | | | R | K | T | | | | | | | | | | | | 3.9 |
| [1] | | | | | | | | | | | | | | N | | | | | G | G | A | | | | | | | | | | | | 4.8 |
| [1] | | | | | | | | | | | | | | N | | | | | R | R | W | | | | | | | | | | | | 4.4 |
| [1] | | | | | | | | | | | | | | N | | | | | G | S | | | | | | | | | | | | | |
| [1] | | | | | | | | | | | | | | Q | | | | | R | N | T | | | | | | | | | | | | 8.7 |
| [2] | | | | | | | | | | | | | | N | | | | | R | H | S | T | N | S | | | | | | | | | 4.0 |
| [2] | | | | | | | | | | | | | | N | | | | | G | T | L | | | | | | | | | | | | 14.8 |
| [1] | | | | | | | | | | | | | | N | | | | | R | G | K | | | | | | | | | | | | 4.4 |
| [1] | | | | | | | | | | | | | | N | | | | | R | G | L | | | | | | | | | | | | 3.9 |
| [1] | | | | | | | | | | | | | | T | | | | | G | R | | | | | | | | | | | | | 3.5 |
| [2] | | | | | | | | | | | | | | N | | | | | R | G | | H | | | | | | | | | | | 5.0 |
| [1] | | | | | | | | | | | | | | | | | | | R | H | G | | | | | | | | | | | | 2.9 |
| [1] | | | | | | | | | | | | | | | | | | | R | G | M | | | | | | | | | | | | 1.0** |
| [7] | | | | | | | | | | | | | | | | | | | | | | | M | W | R | | | | | | | | 1.0** |
| [7] | | | | | | | | | | | | | | | | | | | | | | | F | W | R | | | | | | | | 0.8*** |

TABLE I-continued

| | 1 | | 2 | 3 | | 4 | | | 5 | | | 6 | | | 7 | | 8 | | | |
|---|---|---|---|---|---|---|---|---|---|---|---|---|---|---|---|---|---|---|---|---|
| Human BNP<br>Display BNP | 1<br>S | 2<br>P | 3<br>K<br>D | 4<br>M | 5<br>V | 6<br>Q | 7<br>G | 8<br>S | 9<br>G | 10<br>C | 11<br>F | 12<br>G | 13<br>R | 14<br>K | 15<br>M | 16<br>D | 17<br>R | 18<br>I | 19<br>S | 20<br>S | 21<br>S | 22<br>S | 23<br>G | 24<br>L | 25<br>G | 26<br>C | 27<br>K | 28<br>V | 29<br>L | 30<br>R | 31<br>R | 32<br>H | Binding to NPR-A ratio of mutant/hANP |
| [2] | | | | | | | | | | | | | | | | | | | | | | | M | Y | R | | | | | | | | 2.4 |
| [3] | | | | | | | | | | | | | | | | | | | | | | | L | W | R | | | | | | | | 2.0 |
| [1] | | | | | | | | | | | | | | | | | | | | | | | M | F | R | | | | | | | | 3.0 |
| [1] | | | | | | | | | | | | | | | | | | | | | | | | | | | E | T | | | | | 5.9? |
| [7] | | | | | | | | | | | | | | | | | | | | | | | | | | | P | S | | | | | SRB |
| [3] | | | | | | | | | | | | | | | | | | | | | | | | | | | P | T | | | | | 70.0 |
| [4] | | | | | | | | | | | | | | | | | | | | | | | | | | | N | T | | | | | SRB |
| [1] | | | | | | | | | | | | | | | | | | | | | | | | | | | P | E | P | | | | SRB |
| [1] | | | | | | | | | | | | | | | | | | | | | | | | | | | P | P | S | | | | SRB |
| [1] | | | | | | | | | | | | | | | | | | | | | | | | | | | P | D | P | | | | 1.0** |
| [3] | | | | | | | | | | | | | | | | | | | R | | | | | F | | | | | | E | R | A | SRB |
| [3] | | | | | | | | | | | | | | | | | | | | | | | | F | | | | | | E | | Q | SRB |
| [10] | | | | | | | | | | | | | | | | | | | | | | | | F | | | | | | E | | E | SRB |

SRB = Significantly reduced binding

Example 2

In the following Examples, amino acids are described by the standard three letter amino acid code when referring to intermediates and final products. The linear peptides and intermediates described herein were prepared by the solid phase method of peptide synthesis (R. Merrifield, (1964) J. Am. Chem. Soc. 85:2149 and M. Bodansky, "Principles of Peptide Synthesis." Springer-Verlag, (1984). Abbreviations used are as follows: tert-butyloxycarbonyl (Boc); p-toluenesulfonyl (Tos); 4-methylbenzyl (MeBzl); benzyl (Bzl); 2-bromobenzyloxycarbonyl (Br-Z); cyclohexyl ester (Ochex); 4-methoxylbenzyl (MeOBzl), 2-chlorobenzyloxycarbonyl (Cl-Z); hydrogen fluoride (HF); benzotriazolyloxytris(dimethylamino) phosphoniumhexafluorophosphate (BOP); methylene chloride (DCM); trifluoroacetic acid (TFA); and dimethylacetamide (DMA).

Peptides were assembled using an Applied Biosystems 430A automated peptide synthesizer. Protected amino acids were obtained from various vendors. Side chain protection was Asp (Ochex), Cys (MeOBzl), Arg (Tos), Ser(Bzl), Thr (Bzl), Lys (Cl-Z), and Tyr (Br-Z).

The peptides were assembled on 0.7 g (1.0 mmol) of Boc-Tyr(Br-Z) PAM resin (Applied Biosystems). The coupling protocols were those recommended by Applied Biosystems and DMA was used instead of DMF as solvent. After chain assembly the N-terminal Boc group was removed using TFA. The peptide resin was then washed with dichloromethane followed by methanol and then dried under vacuum. The peptide was then deprotected and removed from the resin by stirring the peptide-resin in 20 ml of a mixture of HF (92.5%), anisole (5%) and ethylmethylsulfide (2.5%) for 1 hr at 0 degrees. The HF was then removed in vacuo and the resin washed with ether. The resin was washed with 10% acetic acid in water, acetonitrile, water, and the filtrate was recovered and lyophilized. The crude linear peptide (300 mg) was dissolved in 10 L of distilled water with the pH adjusted to 7.4–7.6 with concentrated ammonium hydroxide.

The cyclization was begun immediately by adding 0.003M $K_3[Fe(CN)_6]$ (1 g dissolved in 100 mL of distilled water) dropwise (ca. 1 drop/10 sec.) with vigorous stirring. Addition of the iron solution was halted when a bright yellow color persisted, and the reaction mixture was stirred for an additional 4 to 5 h. The pH of the cyclized solution was adjusted to 4.5 with HOAC.

Bio Rex 70 cation exchange resin, 200–400 mesh in the $Na^+$ form was washed with 1 N HCl and then with distilled water. Approximately 110 g of this resin was added to the cyclized peptide solution and stirred overnight. The resin was filtered, washed exhaustively with distilled water, and slurry packed into a column. The peptide was eluted using 70% aqueous HOAc, identified by TLC (ninhydrin visualization) and lyophilized. The peptide was dissolved in 0.1% TFA in water, loaded onto a 2.5 cm×50 cm C-18 reversed phase column (15 micron, 300A) and eluted with a shallow gradient of increasing acetonitrile. The elution conditions consisted of a 10% to 50% acetonitrile (containing 0.1% TFA) gradient at 0.5% min.$^{-1}$. The aqueous phase was 0.1% TFA in water. Product containing fractions were then lyophilized to afford the pure title peptide.

Following the procedure in Example 1, the compounds of Examples 3–6 were analogously prepared.

Example 3

Ser-Pro-Lys-Met-Val-Gln-Gly-Ser-Gly-Cys-Phe-Gly-Arg-Lys-Met-Glu-Arg-Ile-Ser-Ser-Ser-Ser-Phe-Trp-Arg-Cys-Lys-Val-Leu-Arg-Arg-His (SEQ ID NO:2)

Example 4

Ser-Pro-Lys-Met-Val-Gln-Gly-Ser-Gly-Cys-Phe-Gly-Arg-Lys-Met-Glu-Arg-Ile-Arg-Ser-Ser-Ser-Gly-Leu-Gly-Cys-Lys-Val-Leu-Arg-Arg-His (SEQ ID NO:4)

Example 5

Ser-Pro-Lys-Met-Val-Gln-Gly-Ser-Gly-Cys-Phe-Gly-Arg-Lys-Met-Glu-Arg-Ile-Arg-Ser-Ser-Ser-Phe-Trp-Arg-Cys-Lys-Val-Leu-Arg-Arg-His (SEQ ID NO:7)

Example 6

Ser-Pro-Lys-Met-Val-Gln-Gly-Ser-Gly-Cys-Phe-Gly-Gly-Arg-Met-Glu-Arg-Ile-Arg-Ser-Ser-Ser-Gly-Leu-Gly-Cys-Lys-Val-Leu-Arg-Arg-His (SEQ ID NO:43)

Example 6

Measurement of binding affinities for NPR-A and NPR-C.

Methods

Membrane Preparation Membranes from stable 293 cell lines expressing NPR-A (Lowe and Fendly (1992) J. Biol. Chem.) or NPR-C (Cunningham et al. (1994) supra) were prepared by removing the cells from tissue culture plates with 0.5MM EDTA in PBS, centrifuging at 225×g, 4° C., and resuspending in 50 mM Hepes Ph7.4, 1 mM EDTA, 1 mM DTT, 250 mM Sucrose, 0.7 µg/ml Pepstatin A, 0.5 µg/ml Leupeptin, 1 mM PMSF, 1 µM Phosphoramidon. The resuspended cells were homogenized for 30 seconds with a Brinkman polytron on setting 5. The homogenate was centrifuged in 30 ml corex tubes in Sorval HB-4 rotor at 400×(1500 rpm) for 10 minutes at 4° C. The supernatant was centrifuged again in screw cap polycarbonate tubes (Beckman 355618) at 100,000×g (31,500 rpm) for 30 minutes, 4° C. in a Beckman TI60 rotor. The pellet was resuspended in 50 mM Hepes, 0.1 mM EDTA, 5.0 mM $MgCl_2$, 100 mM NaCl, 0.7µg/ml Pepstatin A, 0.5 µg/ml Leupeptin, 1 mM PMSF, 1 µM Phosphoramidon and homogenized again with 15 strokes in a Dounce homogenizer (Wheaton 7 ml, #357542). The membranes were passed through a 22 gauge needle several times before aliquoting into eppendorf tubes for storage at −80° C.

Measurement binding affinities for NPR-A and NPR-C Membranes were diluted in 50 mM Hepes, 5 mM $MgCl_2$, 100 mM NaCl, 0.1 mM EDTA, 0.2% BSA, 1 µM Phosphoramidon and added to an equal volume of diluted pure synthetic peptide plus 30 pM $I^{125}$ labeled ratANP (Amersham). The binding was allowed to go for 2 hours at room temperature in 96 well U-bottomed microtiter polypropylene plates (Sigma M-4029) with gentle agitation. The bound hormone was separated from the free using a Packard Filtermate 196 cell harvester and 1% polyethyleneimine-saturated Packard unifilter-96 GF/B plates by vacuum filtration. The plates were dried under vacuum chamber for 10 minutes prior to adding 40 µl Microscint-20 scintillant and counting in a Packard Topcount scintillation counter. Each affinity represents points measured in duplicate within three separate assays.

Results:

| | Assay #1 | |
|---|---|---|
| | NPR-A | NPR-C |
| hANP (SEQ ID NO: 51) | 43.55 ± 12.9 | 198 ± 90.4 |
| hBNP (SEQ ID NO: 1) | 645 ± 298 | 1791 ± 145 |
| hBNP Gly23Phe, Leu24Trp, Gly25Arg (SEQ ID NO: 2) | 378 ± 136 | 9363 ± 2067 |
| hBNP Ser19Arg (SEQ ID NO: 4) | 155 ± 55.3 | 95,498 ± 14,603 |
| hBNP Arg13Gly, Lys14Arg (SEQ ID NO:48) | 43,723 ± 5915 | 13,918 ± 12,901 |
| hBNP Arg13Gly, Lys14Arg, Ser19Arg (SEQ ID NO:49) | 518 ± 72.2 | 28,370 ± 9,654 |
| hANP Net12Ile, Gly20Phe, Leu21Trp, Gly22Arg (SEQ ID NO:50) | 507 ± 118 | 295 ± 56.8 |
| hBNP Ser19Arg, Gly23Phe, Leu24Trp, Gly25Arg (SEQ ID NO: 7) | 287 ± 27 | 172,400 ± 120,096 |
| hANP Gly16Arg (SEQ ID NO: 52) | 17.2 ± 7.6 | 10,601 ± 1271 |

Example 7

The peptides were assayed for stimulation CGMP production.

Whole Cell Stimulation of cGMP Production, and CGMP RIA

Cell Culture: Cells were maintained in F12 (w/o GHT)/Low Glucose DMEM (50/50), 25 mM Hepes pH 7.2, 2 mM Glutamine, 400 micrograms/ml G418 and 10% dialyzed calf serum. Log phase cells were removed from plates with 0.5 mM EDTA in PBS, taken up in media and cell concentration measured with a coulter counter. Cells were plated to 12 well dishes at a density of 300,000 cells/well, 18 to 24 hours prior to stimulation.

Whole Cell Stimulation: Plates were placed on a 37° C. warm plate, media aspirated and 37° C. incubation media added for 10 min. (50/50, 25 mM Hepes pH 7.2, 0.1 mM isobutyl methyl Xanthine, 0.1% (w/v) BSA). The reaction was terminated for control value—see below, or media was aspirated and incubation media with test sample was added. The reaction was continued for 10 min., then 0.5 ml of ice cold 12% Trichloro Acetic Acid was added to stop the reaction and extract the cyclic nucleotides. Plates were quick frozen on a bed of dry ice, thawed and the TCA with cell debris taken into a 12×75 mm disposable glass tube and spun at 2000×G for 10 min. The supernatant was transferred to a fresh glass tube and the TCA removed by extracting 3 times with water saturated Ether. The residual Ether was removed by boiling off at 50° for 20 minutes. The sample is now ready for RIA determination of CGMP content.

RIA: 100 microliters of sample (neat or dilutions thereof) was measured in duplicate. The standard curve was set up with highest concentration of cGMP first. The protocol for Acetylation is followed as described (Biomedical Techniques Inc., Stoughton, Mass.). After overnight incubation, and centrifugation, pellets were counted in an isodata counter. Data was analyzed using a cGMP RIA analysis program on RS/1.

Results

FIGS. 1 and 2 demonstrate the measurement of cGMP production in 293 cells expressing hNPR-A. Wild-type and variants stimulate guanyl cyclase activity in the membrane preparations as measured by cGMP production.

What is claimed is:

1. A BNP variant having a decreased binding affinity for the human clearance receptor compared to human wild-type BNP wherein at least one of amino acids residues Xaa23, Xaa24 or Xaa25 of human wild-type BNP is selected according to the following scheme:

Xaa23 is selected from the group Gly, Met, Leu and Phe, and conservative substitutions thereof;

Xaa24 is selected from the group Leu, Trp, Tyr, and Phe, and conservative substitutions thereof; and Xaa25 is selected from the group Gly and Arg, and conservative substitutions thereof.

2. The BNP variant of claim 1 wherein Xaa23 is Phe.

3. The BNP variant of claim 1 wherein Xaa24 is Trp.

4. The BNP variant of claim 1 wherein Xaa25 Arg.

5. The BNP variant of claim 4 having at least one additional amino acid selected according to the following scheme:

Xaa23 is selected from the group Met, Phe, and Leu;

Xaa24 is selected from the group Trp, Tyr, and Phe.

6. A BNP variant having a decreased binding affinity for the human clearance receptor compared to human wild-type BNP represented by Formula I:

$$
\begin{array}{c}
\text{A---R}_1\text{-Cys-Phe-Gly-Arg-Lys-Met-Asp-Arg-Ile} \\
\phantom{\text{A---R}_1\text{-}}| \phantom{aaaaaaaaaaaaaaaaaaaaaaaaaaaaaaa} | \\
\phantom{\text{A---R}_1\text{-}}\text{S---S} \phantom{aaaaaaaaaaaaaaaaaaaaaaaaaaaa} | \\
\phantom{\text{A---R}_1\text{-}}| \phantom{aaaaaaaaaaaaaaaaaaaaaaaaaaaaaaa} | \\
\text{B---R}_2\text{-Cys-Xaa}_{25}\text{-Xaa}_{24}\text{-Xaa}_{23}\text{-Ser-Ser-Ser-Xaa}_{19}
\end{array} \quad (I)
$$

wherein:

A is selected from the group consisting of H, $C_1$–$C_6$ alkanoyl and Thr-Ala-Pro-Arg (SEQ ID NO:30);

$R_1$ is absent or selected from the group consisting of, an amino acid and a peptide from between 2 and 10 amino acids;

Xaa19 is selected from the group consisting of Arg, Ala, Asn, Gly and Ser;

$Xaa_{23}$ is selected from the group Met, Phe, Leu and Nle;

$Xaa_{24}$ is selected from the group Trp, Tyr and Phe;

$Xaa_{25}$ is selected from the group and Arg;

$R_2$ is a peptide of 1 to 6 amino acids; and

B is selected from $OR_3$ and $NR_3R_4$ where $R_3$ and $R_4$ are independently selected from H, $C_1$–$C_6$alkyl, $C_6$–$C_{12}$aryl and $C_6$–$C_{12}$aryl-$C_1$–$C_6$alkyl.

7. The BNP variant of claim 6 having the following formula:

Ser-Pro-Lys-Met-Val-Gln-Gly-Ser-Gly-Cys-Phe-Gly-Arg-Lys-Met-[Glu]Asp-Arg-Ile-Ser-Ser-Ser-Ser-Phe-Trp-Arg-Cys-Lys-Val-Leu-Arg-Arg-His (SEQ ID NO:2).

8. The BNP variant of claim 6 having the following formula:

Ser-Pro-Lys-Met-Val-Gln-Gly-Ser-Gly-Cys-Phe-Gly-Arg-Lys-Met-Asp-Arg-Ile-Ser-Ser-Ser-Ser-Met-Trp-Arg-Cys-Lys-Val-Leu-Arg-Arg-His (SEQ ID NO:3).

9. The BNP variant of claim 6 having the following formula:

Ser-Pro-Lys-Met-Val-Gln-Gly-Ser-Gly-Cys-Phe-Gly-Arg-Lys-Met-Asp-Arg-Ile-Arg-Ser-Ser-Ser-Gly-Leu-Gly-Cys-Lys-Val-Leu-Arg-Arg-His (SEQ ID NO:4).

10. The BNP variant of claim 6 having the following formula:

Ser-Pro-Lys-Met-Val-Gln-Gly-Ser-Gly-Cys-Phe-Gly-Arg-Lys-Met-Asp-Arg-Ile-Arg-Ser-Ser-Ser-Phe-Trp-Arg-Cys-Lys-Val-Leu-Arg-Arg-His (SEQ ID NO:7).

11. The BNP variant of claim 7 having the following formula:

Ser-Pro-Lys-Met-Val-Gln-Gly-Ser-Gly-Cys-Phe-Gly-Arg-Lys-Met-Asp-Arg-Ile-Arg-Ser-Ser-Ser-Met-Trp-Arg-Cys-Lys-Val-Leu-Arg-Arg-His (SEQ ID NO:8).

12. A composition comprising a sterile excipient and the BNP variant of claim 1.

13. A method of treating a disorder of electrolyte balance in a mammal comprising administering a pharmaceutically effective amount of the composition of claim 12 to the mammal.

14. A method for inducing natriuresis, diuresis or vasodilation comprising administering to a mammal in need thereof a pharmaceutically effective amount of the composition of claim 12.

* * * * *

UNITED STATES PATENT AND TRADEMARK OFFICE
CERTIFICATE OF CORRECTION

PATENT NO. : 6,028,055

DATED : Feb. 22, 2000

INVENTOR(S) : Lowe et al.

It is certified that error appears in the above-identified patent and that said Letters Patent is hereby corrected as shown below:

On the title page: Item [73], please replace "Genetech, Inc." with -- Genentech, Inc.--.

Signed and Sealed this

Thirtieth Day of January, 2001

Attest:

Q. TODD DICKINSON

*Attesting Officer*      *Director of Patents and Trademarks*

SEQUENCE LISTING (1) GENERAL INFORMATION:

(iii) NUMBER OF SEQUENCES: 52

(2) INFORMATION FOR SEQ ID NO:1:

(i) SEQUENCE CHARACTERISTICS:
       (A) LENGTH: 32 amino acids
       (B) TYPE: Amino Acid
       (D) TOPOLOGY: Linear (xi) SEQUENCE DESCRIPTION: SEQ ID NO:1:

Ser Pro Lys Met Val Gln Gly Ser Gly Cys Phe Gly Arg Lys Met
 1               5                  10                  15

Glu Arg Ile Ser Ser Ser Ser Gly Leu Gly Cys Lys Val Leu Arg
                20                  25                  30

Arg His
    32

```
(2) INFORMATION FOR SEQ ID NO:2:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:2:

Ser Pro Lys Met Val Gln Gly Ser Gly Cys Phe Gly Arg Lys Met
 1               5                  10                  15

Glu Arg Ile Ser Ser Ser Ser Phe Trp Arg Cys Lys Val Leu Arg
                20                  25                  30

Arg His
     32

(2) INFORMATION FOR SEQ ID NO:3:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:3:

Ser Pro Lys Met Val Gln Gly Ser Gly Cys Phe Gly Arg Lys Met
 1               5                  10                  15

Glu Arg Ile Ser Ser Ser Ser Met Trp Arg Cys Lys Val Leu Arg
                20                  25                  30

Arg His
     32

(2) INFORMATION FOR SEQ ID NO:4:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:4:

Ser Pro Lys Met Val Gln Gly Ser Gly Cys Phe Gly Arg Lys Met
 1               5                  10                  15

Glu Arg Ile Arg Ser Ser Gly Leu Gly Cys Lys Val Leu Arg
                20                  25                  30

Arg His
     32

(2) INFORMATION FOR SEQ ID NO:5:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:5:

Ser Pro Lys Met Val Gln Gly Ser Gly Cys Phe Gly Arg Lys Met
 1               5                  10                  15

Glu Arg Ile Arg His Ser Ser Gly Leu Gly Cys Lys Val Leu Arg
                20                  25                  30

Arg His
     32
```

(2) INFORMATION FOR SEQ ID NO:6:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:6:

Ser Pro Lys Met Val Gln Gly Ser Gly Cys Phe Gly Arg Lys Met
 1               5                  10                  15

Glu Arg Ile Arg His Leu Ser Gly Leu Gly Cys Lys Val Leu Arg
                20                  25                  30

Arg His
     32

(2) INFORMATION FOR SEQ ID NO:7:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:7:

Ser Pro Lys Met Val Gln Gly Ser Gly Cys Phe Gly Arg Lys Met
 1               5                  10                  15

Glu Arg Ile Arg Ser Ser Ser Phe Trp Arg Cys Lys Val Leu Arg
                20                  25                  30

Arg His
     32

(2) INFORMATION FOR SEQ ID NO:8:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:8:

Ser Pro Lys Met Val Gln Gly Ser Gly Cys Phe Gly Arg Lys Met
 1               5                  10                  15

Glu Arg Ile Arg Ser Ser Ser Met Trp Arg Cys Lys Val Leu Arg
                20                  25                  30

Arg His
     32

(2) INFORMATION FOR SEQ ID NO:9:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:9:

Ser Pro Lys Met Val Gln Gly Ser Gly Cys Phe Gly Arg Lys Met
 1               5                  10                  15

Glu Arg Ile Arg His Ser Ser Met Trp Arg Cys Lys Val Leu Arg
                20                  25                  30

Arg His
     32

(2) INFORMATION FOR SEQ ID NO:10:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:10:

Ser Pro Lys Met Val Gln Gly Ser Gly Cys Phe Gly Arg Lys Met
1               5                   10                  15

Glu Arg Ile Arg His Leu Ser Met Trp Arg Cys Lys Val Leu Arg
                20                  25                  30

Arg His
    32

(2) INFORMATION FOR SEQ ID NO:11:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:11:

Ser Pro Lys Met Val Gln Gly Ser Gly Cys Phe Gly Ser Pro Met
1               5                   10                  15

Glu Arg Ile Arg Ser Ser Ser Gly Leu Gly Cys Lys Val Leu Arg
                20                  25                  30

Arg His
    32

(2) INFORMATION FOR SEQ ID NO:12:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:12:

Ser Pro Lys Met Val Gln Gly Ser Gly Cys Phe Gly Arg Thr Met
1               5                   10                  15

Glu Arg Ile Arg Ser Gln Ser Gly Leu Gly Cys Lys Val Leu Arg
                20                  25                  30

Arg His
    32

(2) INFORMATION FOR SEQ ID NO:13:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:13:

Ser Pro Lys Met Val Gln Gly Ser Gly Cys Phe Gly Arg Asn Met
1               5                   10                  15

Glu Arg Ile Arg His Leu Ser Gly Leu Gly Cys Lys Val Leu Arg
                20                  25                  30

Arg His
    32

(2) INFORMATION FOR SEQ ID NO:14:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:14:

Ser Pro Lys Met Val Gln Gly Ser Gly Cys Phe Gly Arg Asn Met
 1               5                  10                  15

Glu Arg Ile Ala Arg Glu Ser Gly Leu Gly Cys Lys Val Leu Arg
                20                  25                  30

Arg His
     32

(2) INFORMATION FOR SEQ ID NO:15:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:15:

Ser Pro Lys Met Val Gln Gly Ser Gly Cys Phe Gly Arg Asn Met
 1               5                  10                  15

Glu Arg Ile Arg Lys Thr Ser Gly Leu Gly Cys Lys Val Leu Arg
                20                  25                  30

Arg His
     32

(2) INFORMATION FOR SEQ ID NO:16:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:16:

Ser Pro Lys Met Val Gln Gly Ser Gly Cys Phe Gly Arg Asn Met
 1               5                  10                  15

Glu Arg Ile Arg Gly Ser Ser Gly Leu Gly Cys Lys Val Leu Arg
                20                  25                  30

Arg His
     32

(2) INFORMATION FOR SEQ ID NO:17:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:17:

Ser Pro Lys Met Val Gln Gly Ser Gly Cys Phe Gly Arg Asn Met
 1               5                  10                  15

Glu Arg Ile Gly Arg Ala Ser Gly Leu Gly Cys Lys Val Leu Arg
                20                  25                  30

Arg His
     32

(2) INFORMATION FOR SEQ ID NO:18:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:18:

Ser Pro Lys Met Val Gln Gly Ser Gly Cys Phe Gly Arg Asn Met
 1               5                  10                  15

Glu Arg Ile Arg Trp Ser Ser Gly Leu Gly Cys Lys Val Leu Arg
                20                  25                  30

Arg His
     32

(2) INFORMATION FOR SEQ ID NO:19:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:19:

Ser Pro Lys Met Val Gln Gly Ser Gly Cys Phe Gly Arg Asn Met
 1               5                  10                  15

Glu Arg Ile Arg Asn Thr Ser Gly Leu Gly Cys Lys Val Leu Arg
                20                  25                  30

Arg His
     32

(2) INFORMATION FOR SEQ ID NO:20:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:20:

Ser Pro Lys Met Val Gln Gly Ser Gly Cys Phe Gly Arg Gln Met
 1               5                  10                  15

Glu Arg Ile Arg His Ser Thr Gly Leu Gly Cys Lys Val Leu Arg
                20                  25                  30

Arg His
     32

(2) INFORMATION FOR SEQ ID NO:21:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:21:

Ser Pro Lys Met Val Gln Gly Ser Gly Cys Phe Gly Arg Asn Met
 1               5                  10                  15

Glu Arg Ile Gly His Leu Ser Gly Leu Gly Cys Lys Val Leu Arg
                20                  25                  30

Arg His
     32

(2) INFORMATION FOR SEQ ID NO:22:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:22:

```
Ser Pro Lys Met Val Gln Gly Ser Gly Cys Phe Gly Arg Asn Met
 1               5                  10                  15

Glu Arg Ile Arg Thr Lys Ser Gly Leu Gly Cys Lys Val Leu Arg
                20                  25                  30

Arg His
     32
```

(2) INFORMATION FOR SEQ ID NO:23:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:23:

```
Ser Pro Lys Met Val Gln Gly Ser Gly Cys Phe Gly Arg Asn Met
 1               5                  10                  15

Glu Arg Ile Gly Gly Leu Ser Gly Leu Gly Cys Lys Val Leu Arg
                20                  25                  30

Arg His
     32
```

(2) INFORMATION FOR SEQ ID NO:24:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:24:

```
Ser Pro Lys Met Val Gln Gly Ser Gly Cys Phe Gly Arg Asn Met
 1               5                  10                  15

Glu Arg Ile Arg Ser Ser Ser Gly Leu Gly Cys Lys Val Leu Arg
                20                  25                  30

Arg His
     32
```

(2) INFORMATION FOR SEQ ID NO:25:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:25:

```
Ser Pro Lys Met Val Gln Gly Ser Gly Cys Phe Gly Arg Thr Met
 1               5                  10                  15

Glu Arg Ile Arg His Gly Gly Leu Gly Cys Lys Val Leu Arg
                20                  25                  30

Arg His
     32
```

(2) INFORMATION FOR SEQ ID NO:26:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:26:

```
Ser Pro Lys Met Val Gln Gly Ser Gly Cys Phe Gly Arg Asn Met
 1               5                  10                  15

Glu Arg Ile Arg Gly Met Ser Gly Leu Gly Cys Lys Val Leu Arg
                20                  25                  30

Arg His
    32
```

(2) INFORMATION FOR SEQ ID NO:27:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:27:

```
Ser Pro Lys Met Val Gln Gly Ser Gly Cys Phe Gly Arg Lys Met
 1               5                  10                  15

Glu Arg Ile Ser Ser Ser Ser Met Tyr Arg Cys Lys Val Leu Arg
                20                  25                  30

Arg His
    32
```

(2) INFORMATION FOR SEQ ID NO:28:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:28:

```
Ser Pro Lys Met Val Gln Gly Ser Gly Cys Phe Gly Arg Lys Met
 1               5                  10                  15

Glu Arg Ile Ser Ser Ser Ser Leu Trp Arg Cys Lys Val Leu Arg
                20                  25                  30

Arg His
    32
```

(2) INFORMATION FOR SEQ ID NO:29:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:29:

```
Ser Pro Lys Met Val Gln Gly Ser Gly Cys Phe Gly Arg Lys Met
 1               5                  10                  15

Glu Arg Ile Ser Ser Ser Ser Met Phe Arg Cys Lys Val Leu Arg
                20                  25                  30

Arg His
    32
```

```
(2) INFORMATION FOR SEQ ID NO:30:

(i) SEQUENCE CHARACTERISTICS:
         (A) LENGTH: 4 amino acids
         (B) TYPE: Amino Acid
         (D) TOPOLOGY: Linear (xi) SEQUENCE DESCRIPTION: SEQ ID NO:30:

Thr Ala Pro Arg
 1           4

(2) INFORMATION FOR SEQ ID NO:31:

(i) SEQUENCE CHARACTERISTICS:
         (A) LENGTH: 5 amino acids
         (B) TYPE: Amino Acid
         (D) TOPOLOGY: Linear (xi) SEQUENCE DESCRIPTION: SEQ ID NO:31:

Val Gln Gly Ser Gly
 1               5

(2) INFORMATION FOR SEQ ID NO:32:

(i) SEQUENCE CHARACTERISTICS:
         (A) LENGTH: 9 amino acids
         (B) TYPE: Amino Acid
         (D) TOPOLOGY: Linear (xi) SEQUENCE DESCRIPTION: SEQ ID NO:32:

Ser Pro Lys Met Val Gln Gly Ser Gly
 1               5               9

(2) INFORMATION FOR SEQ ID NO:33:

(i) SEQUENCE CHARACTERISTICS:
         (A) LENGTH: 6 amino acids
         (B) TYPE: Amino Acid
         (D) TOPOLOGY: Linear (xi) SEQUENCE DESCRIPTION: SEQ ID NO:33:

Lys Val Leu Arg Arg His
 1               5   6

(2) INFORMATION FOR SEQ ID NO:34:

(i) SEQUENCE CHARACTERISTICS:
         (A) LENGTH: 4 amino acids
         (B) TYPE: Amino Acid
         (D) TOPOLOGY: Linear (xi) SEQUENCE DESCRIPTION: SEQ ID NO:34:

Xaa Xaa Ser Gly
 1           4

(2) INFORMATION FOR SEQ ID NO:35:

(i) SEQUENCE CHARACTERISTICS:
         (A) LENGTH: 5 amino acids
         (B) TYPE: Amino Acid
         (D) TOPOLOGY: Linear (xi) SEQUENCE DESCRIPTION: SEQ ID NO:35:

Xaa Xaa Xaa Ser Gly
 1               5
```

```
(2) INFORMATION FOR SEQ ID NO:36:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:36:

Xaa Xaa Xaa Xaa Ser Gly
  1           5   6

(2) INFORMATION FOR SEQ ID NO:37:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:37:

Lys Xaa Xaa Xaa Xaa Ser Gly
  1           5       7

(2) INFORMATION FOR SEQ ID NO:38:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:38:

Pro Lys Xaa Xaa Xaa Xaa Ser Gly
  1           5           8

(2) INFORMATION FOR SEQ ID NO:39:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO:39:

Ser Pro Lys Xaa Xaa Xaa Xaa Ser Gly
  1           5               9

(2) INFORMATION FOR SEQ ID NO:40:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:40:

Xaa Val Leu Arg
  1           4

(2) INFORMATION FOR SEQ ID NO:41:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:41:

Xaa Val Leu Arg Xaa
  1           5
```

(2) INFORMATION FOR SEQ ID NO:42:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:42:

```
Xaa Val Leu Arg Xaa Tyr His
 1           5       7
```

(2) INFORMATION FOR SEQ ID NO:43:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:43:

```
Ser Pro Lys Met Val Gln Gly Ser Gly Cys Phe Gly Gly Arg Met
 1           5                  10                      15

Glu Arg Ile Arg Ser Ser Ser Gly Leu Gly Cys Lys Val Leu Arg
             20                  25                      30

Arg His
     32
```

(2) INFORMATION FOR SEQ ID NO:44:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:44:

```
Ser Pro Lys Met Met His Lys Ser Gly Cys Phe Gly Arg Arg Leu
 1           5                  10                      15

Asp Arg Ile Gly Ser Leu Ser Gly Leu Gly Cys Asn Val Leu Arg
             20                  25                      30

Lys Tyr
     32
```

(2) INFORMATION FOR SEQ ID NO:45:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:45:

```
Ser Pro Lys Thr Met Arg Asp Ser Gly Cys Phe Gly Arg Arg Leu
 1           5                  10                      15

Asp Arg Ile Gly Ser Leu Ser Gly Leu Gly Cys Asn Val Leu Arg
             20                  25                      30

Arg Tyr
     32
```

(2) INFORMATION FOR SEQ ID NO:46:

(i) SEQUENCE CHARACTERISTICS:
        (A) LENGTH: 45 amino acids
        (B) TYPE: Amino Acid
        (D) TOPOLOGY: Linear (xi) SEQUENCE DESCRIPTION: SEQ ID NO:46:

```
Ser Gln Asp Ser Ala Phe Arg Ile Gln Glu Arg Leu Arg Asn Ser
  1               5                  10                  15

Lys Met Ala His Ser Ser Cys Phe Gly Gln Lys Ile Asp Arg
                20                  25                  30

Ile Gly Ala Val Ser Arg Leu Gly Cys Asp Gly Leu Arg Leu Phe
                35                  40                  45
```

(2) INFORMATION FOR SEQ ID NO:47:

(i) SEQUENCE CHARACTERISTICS:
        (A) LENGTH: 45 amino acids
        (B) TYPE: Amino Acid
        (D) TOPOLOGY: Linear (xi) SEQUENCE DESCRIPTION: SEQ ID NO:47:

```
Ser Gln Gly Ser Thr Leu Arg Val Gln Gln Arg Pro Gln Asn Ser
  1               5                  10                  15

Lys Val Thr His Ile Ser Ser Cys Phe Gly His Lys Ile Asp Arg
                20                  25                  30

Ile Gly Ser Val Ser Arg Leu Gly Cys Asn Ala Leu Lys Leu Leu
                35                  40                  45
```

(2) INFORMATION FOR SEQ ID NO:48:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:48:

```
Ser Pro Lys Met Val Gln Gly Ser Gly Cys Phe Gly Gly Arg Met
  1               5                  10                  15

Asp Arg Ile Ser Ser Ser Gly Leu Gly Cys Lys Val Leu Arg
                20                  25                  30

Arg His
    32
```

(2) INFORMATION FOR SEQ ID NO:49:

(i) SEQUENCE CHARACTERISTICS:
        (A) LENGTH: 32 amino acids
        (B) TYPE: Amino Acid
        (D) TOPOLOGY: Linear (xi) SEQUENCE DESCRIPTION: SEQ ID NO:49:

```
Ser Pro Lys Met Val Gln Gly Ser Gly Cys Phe Gly Gly Arg Met
  1               5                  10                  15

Asp Arg Ile Arg Ser Ser Gly Leu Gly Cys Lys Val Leu Arg
                20                  25                  30

Arg His
    32
```

(2) INFORMATION FOR SEQ ID NO:50:

(i) SEQUENCE CHARACTERISTICS:
        (A) LENGTH: 28 amino acids
        (B) TYPE: Amino Acid
        (D) TOPOLOGY: Linear (xi) SEQUENCE DESCRIPTION: SEQ ID NO:50:

```
Ser Leu Arg Arg Ser Ser Cys Phe Gly Gly Arg Ile Asp Arg Ile
  1               5                  10                  15
```

```
Gly Ala Gln Ser Phe Trp Arg Cys Asn Ser Phe Arg Tyr
             20                  25          28
```

(2) INFORMATION FOR SEQ ID NO:51:

(i) SEQUENCE CHARACTERISTICS:
        (A) LENGTH: 28 amino acids
        (B) TYPE: Amino Acid
        (D) TOPOLOGY: Linear (xi) SEQUENCE DESCRIPTION: SEQ ID NO:51:

```
Ser Leu Arg Arg Ser Ser Cys Phe Gly Gly Arg Ile Asp Arg Ile
 1           5               10                  15

Gly Ala Gln Ser Gly Leu Gly Cys Asn Ser Phe Arg Tyr
             20                  25          28
```

(2) INFORMATION FOR SEQ ID NO:52:

(i) SEQUENCE CHARACTERISTICS:
        (A) LENGTH: 28 amino acids
        (B) TYPE: Amino Acid
        (D) TOPOLOGY: Linear (xi) SEQUENCE DESCRIPTION: SEQ ID NO:52:

```
Ser Leu Arg Arg Ser Ser Cys Phe Gly Gly Arg Ile Asp Arg Ile
 1           5               10                  15

Arg Ala Gln Ser Gly Leu Gly Cys Asn Ser Phe Arg Tyr
             20                  25          28
```